US010098866B2

(12) United States Patent
Ishida et al.

(10) Patent No.: US 10,098,866 B2
(45) Date of Patent: Oct. 16, 2018

(54) PHARMACEUTICAL PREPARATION CONTAINING COPOLYVIDONE

(71) Applicant: Takeda Pharmaceutical Company Limited, Osaka (JP)

(72) Inventors: Hajime Ishida, Osaka (JP); Makoto Fukuta, Nara (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/234,604

(22) Filed: Aug. 11, 2016

(65) Prior Publication Data

US 2017/0020841 A1 Jan. 26, 2017

Related U.S. Application Data

(63) Continuation of application No. 12/459,551, filed on Jul. 1, 2009, now abandoned, which is a continuation of application No. 10/416,172, filed as application No. PCT/JP01/10016 on Nov. 16, 2001, now abandoned.

(30) Foreign Application Priority Data

Nov. 17, 2000 (JP) ................ 2000-351223

(51) Int. Cl.
| | |
|---|---|
| *A61K 31/343* | (2006.01) |
| *A61K 9/28* | (2006.01) |
| *A61K 31/137* | (2006.01) |
| *A61K 31/352* | (2006.01) |
| *A61K 31/36* | (2006.01) |
| *A61K 31/407* | (2006.01) |
| *A61K 47/32* | (2006.01) |
| *C07D 307/93* | (2006.01) |

(52) U.S. Cl.
CPC ............ *A61K 31/343* (2013.01); *A61K 9/284* (2013.01); *A61K 9/2813* (2013.01); *A61K 9/2866* (2013.01); *A61K 31/137* (2013.01); *A61K 31/352* (2013.01); *A61K 31/36* (2013.01); *A61K 31/407* (2013.01); *A61K 47/32* (2013.01); *C07D 307/93* (2013.01)

(58) Field of Classification Search
None
See application file for complete search history.

(56) References Cited

U.S. PATENT DOCUMENTS

| | | | | | |
|---|---|---|---|---|---|
| 4,999,226 | A | * | 3/1991 | Schock | A61K 9/209 424/471 |
| 5,401,562 | A | * | 3/1995 | Akao | B32B 27/10 428/211.1 |
| 5,595,762 | A | * | 1/1997 | Derrieu | A61K 8/676 424/490 |
| 6,004,582 | A | | 12/1999 | Faour et al. | |
| 6,034,239 | A | | 3/2000 | Ohkawa et al. | |
| 6,054,482 | A | | 4/2000 | Augart et al. | |
| 6,248,359 | B1 | | 6/2001 | Faour | |
| 6,310,107 | B1 | | 10/2001 | Kato et al. | |
| 6,348,485 | B1 | * | 2/2002 | Ohkawa | A61K 31/435 514/215 |
| 6,432,448 | B1 | * | 8/2002 | Augello | A61K 9/286 424/474 |
| 2001/0007680 | A1 | * | 7/2001 | Kolter | A61K 9/0056 424/482 |
| 2001/0048943 | A1 | | 12/2001 | Faour et al. | |
| 2003/0219483 | A1 | | 11/2003 | Faour et al. | |

FOREIGN PATENT DOCUMENTS

| | | | |
|---|---|---|---|
| DE | 1617328 A1 | | 6/1971 |
| HU | 54035 | | 6/1989 |
| JP | 456558 | | 12/1966 |
| WO | 9732871 A1 | | 9/1997 |
| WO | WO 97/32871 | * | 9/1997 |
| WO | 9838156 A1 | | 9/1998 |
| WO | 9853802 A1 | | 12/1998 |
| WO | 99/59572 A1 | | 11/1999 |
| WO | 0149267 A1 | | 7/2001 |
| WO | 0151041 A1 | | 7/2001 |

OTHER PUBLICATIONS

Database WPI Week 199109 Thompson Scientific, London, GB; AN 1991-060234 XP002620214.
Extended European Search Report dated Feb. 17, 2011 (9 pages).
ISP Japanese Catalogue and English version from Website.
Kollidon VA 64, BASF, Jun. 1996, pp. 1-8.
English Translation of HU54035; "Method for coating medicinal substances tending to decompose for preventing them against moisture and oxygen", pp. 1-11.
Okano, T., "Shin-Yakuzai-Gaku Souron", Nankoudo (3rd revised ed.), (1987), pp. 143-144.

* cited by examiner

*Primary Examiner* — Robert A Wax
*Assistant Examiner* — Danah Al-Awadi
(74) *Attorney, Agent, or Firm* — Mintz Levin Cohn Ferris Glovsky and Popeo, P.C.; David G. Conlin; Nicholas A. Zachariades

(57) ABSTRACT

A stabilized preparation which comprises: a unstable drug in a polyethylene glycol-containing preparation; and a coating agent comprising a copolyvidone instead of polyethylene glycol with which the drug is coated.

15 Claims, No Drawings

PHARMACEUTICAL PREPARATION CONTAINING COPOLYVIDONE

CROSS REFERENCE TO RELATED APPLICATIONS

This application is a continuation of U.S. Ser. No. 12/459,551, filed Jul. 1, 2009, pending, which is a continuation of U.S. Ser. No. 10/416,172, filed May 8, 2003, abandoned, which is the United States National Phase filing of International Patent Application No. PCT/JP01/10016, filed 16 Nov. 2001, which claims priority of Japanese application 2000-351223, filed 17 Nov. 2000, the disclosures of all of which are incorporated herein by reference.

TECHNICAL FIELD

The present invention relates to a preparation, particularly a pharmaceutical preparation which is coated with a coating agent containing copolyvidone and is superior in storage stability, and the like.

BACKGROUND ART

Tablets used commonly as oral preparations are formed by using various additives such as diluents, binders, lubricants, disintegrators, etc. Depending on an active compound, some tablets are less stable to light during circulation and storage and these tablets are often provided with a coating film capable of exerting a light protecting effect by film coating. It is also a useful means to form a coating film in order to prevent bitterness of a drug. This coating film is generally composed of hydroxypropylmethylcellulose (HPMC) or hydroxypropylcellulose (HPC) as water-soluble coating film agents, polyethylene glycol (PEG) as plasticizers and titanium dioxide as light-protecting agents and, if necessary, iron sesquioxide such as colorants.

OBJECTS OF THE INVENTION

Tablets essentially require the addition of plasticizers in order to increase the film strength and to improve the plasticity during the process and appearance, and polyethylene glycol is generally used as plasticizers of a water-soluble coating agent.

However, depending on an active compound such as a pharmaceutically active ingredient, the stability of a base drug to heat or light is impaired by the addition of polyethylene glycol, thereby causing such a problem in the preparation that the activity cannot be maintained for a sufficient period even in a normal storage state in the medical field.

SUMMARY OF THE INVENTION

To achieve the above object, the present inventors have intensively studied about plasticizers, which can be used in place of polyethylene glycol, and found surprisingly that copolyvidone known as a film-forming additive is a useful plasticizer which does not impair the stability of the active compound and can be used in place of polyethylene glycol, and thus the present invention has been completed based on this finding.

The present invention provides:

(1) A stabilized preparation comprising a unstable drug in a polyethylene glycol-containing preparation and a copolyvidone-containing coating agent (free from polyethylene glycol) with which the drug is coated;

(2) The preparation according to (1), wherein the drug is a unstable drug in a preparation coated with a polyethylene glycol-containing coating agent;

(3) The preparation according to (1), wherein the coating agent contains a water-soluble polymer;

(4) The preparation according to (1), wherein the coating agent further contains a light-protecting agent;

(5) The preparation according to claim 1, wherein the unstable drug in the polyethylene glycol-containing preparation is a compound represented by the formula:

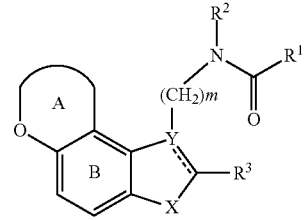

wherein $R^1$ represents an optionally substituted hydrocarbon group, an optionally substituted amino group or an optionally substituted heterocyclic group,
$R^2$ represents a hydrogen atom or an optionally substituted hydrocarbon group,
$R^3$ represents a hydrogen atom, an optionally substituted hydrocarbon group, or an optionally substituted heterocyclic group,
X represents $CHR^4$, $NR^4$, O or S ($R^4$ represents a hydrogen atom or an optionally substituted hydrocarbon group),
Y represents C, CH or N (provided that, when X represents $CH_2$, Y is C or CH),
≡≡≡ represents a single bond or a double bond, ring A represents an optionally substituted 5- to 7-membered heterocyclic ring containing an oxygen atom, ring B represents an optionally substituted benzene ring, and
m represents an integer of 1 to 4, or a salt thereof;

(6) The preparation according to (1), wherein the unstable drug in the polyethylene glycol-containing preparation is a compound represented by the formula:

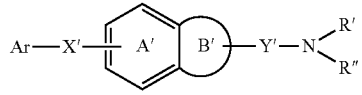

wherein Ar represents an optionally substituted aromatic group, X' represents a divalent $C_{1-6}$ aliphatic hydrocarbon group which optionally have 1 or 2 divalent groups selected from —O—, —S—, —CO—, —SO—, —$SO_2$— and —COO—, Y' represents a divalent $C_{1-6}$ aliphatic hydrocarbon group, R' and R" are the same or different and each represents a hydrogen atom or an optionally substituted $C_{1-6}$ alkyl, ring A' represents a benzene ring which may be further substituted, and ring B' represents a 4- or 8-membered ring which may be further substituted, or a salt thereof;

(7) The preparation according to (1), wherein the unstable drug in the polyethylene glycol-containing preparation is selected from N-[2-(1,6,7,8-tetrahydro-2H-indeno[5,4-b]furan-8-yl)ethyl]acetylamide, N-[2-(1,6,7,8-tetrahydro-2H-indeno[5,4-b]furan-8-yl)ethyl]propionamide, N-[2-(1,6,7,8-tetrahydro-2H-indeno[5,4-b]furan-8-yl)ethyl]butylamide, 6-(4-biphenylyl)methoxy-2-[2-(N,N-dimethylamino)ethyl]tetralin, 6-(4-biphenylyl)methoxy-2-(N,N-dimethylamino)

methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, (+)-6-(4-biphenylyl)methoxy-2-[2-(N,N-dimethylamino)ethyl]tetralin, (+)-6-(4-biphenylyl)methoxy-2-[2-(N,N-diethylamino)ethyl]tetralin, (+)-2-[2-(N,N-dimethylamino)ethyl]-6-(4'-methylbiphenyl-4-yl)methoxytetralin, (+)-2-[2-(N,N-dimethylamino)ethyl]-6-(4'-methoxybiphenyl-4-yl)methoxytetralin, (+)-6-(2',4'-dimethoxybiphenyl-4-yl)methoxy-2-[2-(N,N-dimethylamino)ethyl]tetralin, (+)-6-[4-(1,3-benzodioxazol-5-yl)phenyl]methoxy-2-[2-(N,N-dimethylamino)ethyl]tetralin, (+)-6-(3',4'-dimethoxybiphenyl-4-yl)methoxy-2-[2-(N,N-dimethylamino)ethyl]tetralin, an optically active substance and a salt thereof;

(8) A method for stabilizing a preparation, which comprises coating a unstable drug in a polyethylene glycol-containing preparation with a coating agent containing copolyvidone;

(9) Use of a copolyvidone-containing coating agent for stabilizing a unstable drug in a polyethylene glycol-containing preparation;

(10) Use of copolyvidone in a coating agent for stabilizing a unstable drug in a polyethylene glycol-containing preparation;

(11) Use of copolyvidone according to claim 10 for stabilizing a unstable drug in a polyethylene glycol-containing preparation in a coating agent; and the like.

DETAILED DESCRIPTION OF THE INVENTION

"Copolyvidone" used in the present invention is described in Japanese Pharmaceutical Excipients and European Pharmacopoeia and is a copolymer of 1-vinyl-2-pyrrolidone and vinyl acetate in a weight ratio of 3:2. Copolyvidone is commercially available [Plasdone S-630 (trade name) ISP, Ltd., Kollidon VA64 (trade name) BASF Ltd.].

The amount of "copolyvidone" in the coating agent is, for example, within a range from about 5 to about 50% by weight, preferably from about 10 to about 30% by weight, and more preferably from about 10 to about 20% by weight.

The "coating agent" used in the present invention contains a coating base, in addition to "copolyvidone". The amount of the coating base in the coating agent is one that is generally used for manufacturing a preparation. Optionally, the "coating agent" can further contain additives which do not adversely effect the coating agent or the pharmaceutical preparation.

The "coating agent" can be a liquid in which each of the above-mentioned ingredients is dissolved or dispersed in water or organic solvent. The kinds of the organic solvent are not limited, and for example, alcohols such as methanol, ethanol, isopropyl alcohol, etc.; ketones such as acetone, etc.; can be used. A mixture of water and an organic solvent also can be used.

The above-mentioned coating base includes, for example, a sugar coating base, a water-soluble film-coating base, an enteric film-coating base, a sustained release film-coating base, etc.

As the sugar coating base, sucrose can be used, and one or more of materials selected from talc, precipitated calcium carbonate, gelatin, acacia, pullulan, carnauba wax, etc., can be used in combination.

The water soluble film-coating base includes, for example, cellulose polymers such as hydroxypropylcellulose, hydroxypropylmethylcellulose, hydroxyethylcellulose, methylhydroxyethylcellulose, etc.; a synthetic polymer such as polyvinylacetal diethylaminoacetate, aminoalkyl methacrylate copolymer E [EUDRAGIT E (trade name), Rohm Pharma Co.], polyvinylpyrrolidone, etc.; a polysaccharide such as pullulan, etc.; etc.

The enteric film-coating base includes, for example, cellulose polymers such as hydroxypropylmethylcellulose phthalate, hydroxypropylmethylcellulose acetate succinate, carboxymethylethylcellulose, cellulose acetate phthalate, etc.; acrylic acid polymers such as methacrylic acid copolymer L [EUDRAGIT L (trade name), Rohm Pharma Co.], methacrylic acid copolymer LD [EUDRAGIT L-30D55 (trade name), Rohm Pharma Co.], methacrylic acid copolymer S [EUDRAGIT S (trade name) Rohm Pharma Co.], etc.; natural compounds such as shellac, etc.; etc.

The sustained release film-coating base includes, for example, cellulose polymers such as ethyl cellulose, etc.; acrylic acid polymers such as aminoalkyl methacrylate copolymer RS [EUDRAGIT RS (trade name), Rohm Pharma Co.], emulsion of ethyl acrylate and methyl methacrylate copolymer [EUDRAGIT NE (trade name), Rohm Pharma Co.], etc.; etc.

Two or more of the above-mentioned coating bases can be used as a mixture in a given ratio.

The coating agent is preferably a water-soluble coating agent in view of the working environment, and preferably contains a water-soluble polymer such as hydroxypropylcellulose, hydroxypropylmethylcellulose, hydroxyethylcellulose, methylhydroxyethylcellulose, etc.

The above-mentioned additives include, for example, light-protecting agents, colorants, flavors, etc., and can be added in the amount generally used in the manufacture of a pharmaceutical preparation.

The light-protecting agents include, for example, oxides of inorganic substances such as titanium dioxide, iron sesquioxide, zinc oxide, etc. The light-protecting agent is preferably metal oxide, and more preferably titanium dioxide. It is also preferred to use talc or barium sulfate as the light-protecting agent in place of titanium dioxide.

The colorants include, for example, a water soluble food tar dye (for example, food red No. 2 or No. 3, food yellow No. 4 or No. 5, food blue No. 1 or No. 2, etc.), a water insoluble lake dye (an aluminum salt of the above-mentioned water soluble food tar dye, etc.) and natural colorants (for example, β-carotene, chlorophyll, etc.), and the like.

The flavors include, for example, lemon oil, orange, dl- or l-menthol, etc.

The "coating agent" in the present invention can be manufactured by mixing the above-mentioned "copolyvidone" and the above-mentioned coating base, if necessary, after adding the above-mentioned additives.

The "coating agent" can also be manufactured by dissolving or dispersing each of the above-mentioned ingredients in water or the above-mentioned organic solvent. A uniform coating can be obtained by such a manufacturing method.

The "preparation" of the present invention is that obtained by coating a "unstable drug in a polyethylene glycol-containing preparation" with the above-mentioned coating agent, in particular pharmaceutical preparation. The "unstable drug in a polyethylene glycol-containing preparation" may be a "drug" alone or a mixture of the "drug" and a conventional "preparation ingredients" used for manufacturing a preparation.

A dosage form of the drug includes, for example, tablets, powders, granules, fine granules, pills, etc.

Although the mechanism of action of unstabilization is not elucidated, the term the "unstable drug in a polyethylene glycol-containing preparation" as used herein refers to a drug which is unstabilized in a polyethylene glycol-containing preparation, especially a preparation coated with a polyethylene glycol-containing coating agent and includes, for example, among drugs mentioned hereinafter, a drug whose amount is reduced by 0.5% by weight or more based on the amount immediately after manufacturing after storage in a dark place at 60° C. for 4 weeks. A more unstable drug means a drug whose amount is reduced by 2% by weight or more after storage under the same conditions. Alternatively, an unstable drug includes a drug wherein an amount of total analogue substances increases by 0.2% by weight or more or an amount of total unreacted substances increases by 0.2% by weight or more.

These drugs include, for example, one or more agents selected from the group consisting of nourishing and health-promoting agents, antipyretic-analgesic-antiinflammatory agents, antipsychotic drugs, antianxiety drugs, antidepressants, hypnotic-sedatives, spasmolytics, central nervous system affecting drugs, cerebral metabolism ameliolators, antiepileptics, sympathomimetic agents, gastrointestinal function conditioning agents, antacids, antiulcer agents, antitussive-expectorants, antiemetics, respiratory stimulants, bronchodilators, antiallergic agents, dental buccal drugs, antihistamines, cardiotonics, antiarrhythmic agents, diuretics, hypotensive agents, vasoconstrictors, coronary vasodilators, peripheral vasodilators, antihyperlipidemic agents, cholagogues, antibiotics, chemotherapeutic agents, agents for treating diabetic, drugs for osteoporosis, skeletal muscle relaxants, antidinics, hormones, alkaloid narcotics, sulfa drugs, antipodagrics, anticoagulants, anti-malignant tumor agents, agents for Alzheimer's disease, etc.

The amount of the "drug" in the "preparation" may be the effective amount of the "drug".

Hereinafter, specific examples of the above-mentioned drugs are described. Since the degree of unstabilization varies depending on particular combination of respective drugs and other preparation ingredients, the following specific examples may include those that require no stabilization.

The nourishing and health-promoting agents include, for example, vitamins such as vitamin A, vitamin D, vitamin E (d-α-tocopherol acetate, etc.), vitamin $B_1$ (dibenzoylthiamine, fursulthiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), vitamin $B_{12}$ (hydroxocobalamin acetate, etc.), etc.; minerals such as calcium, magnesium and iron; proteins, amino acids, oligosaccharides, galenical, etc.

The antipyretic-analgesic-antiinflammatory agents include, for example, aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, serratiopeptidase, lysozyme chloride, tolfenamic acid, mefenamic acid, diclofenac sodium, flufenamic acid, salicylamide, aminopyrine, ketoprofen, indomethacin, bucolome, pentazocine, etc.

The antipsychotic drugs include, for example, chlorpromazine, reserpine, etc.

The antianxiety drugs include, for example, alprazolam, chlordiazepoxide, diazepam, etc.

The antidepressants include, for example, imipramine, maprotiline, amphetamine, etc.

The hypnotic-sedatives include, for example, estazolam, nitrazepam, diazepam, perlapine, phenobarbital sodium, etc.

The spasmolytics include, for example, scopolamine hydrobromide, diphenhydramine hydrochloride, papaverine hydrochloride, etc.

The central nervous system affecting drugs include, for example, citicoline, rotirenine, etc.

The cerebral metabolism ameliolators include, for example, idevenone, vinpocetine, meclofenoxate hydrochloride, 8-[1-oxo-3-[1-(phenylmethyl)piperidine-4-yl]propyl]-2,3,4,5-tetrahydro-1H-1-benzazepine or a salt thereof, etc.

The antiepileptics include, for example, phenytoin, carbamazepine, etc.

The sympathomimetic agents include, for example, isoproterenol hydrochloride, etc.

The gastrointestinal function conditioning agents include, for example, stomachic-digestives such as diastase, saccharated pepsin, scopolia extract, cellulase AP3, lipase AP, cinnamon oil, etc.; intestinal function controlling drugs such as perperine hydrochloride, resistant lactic acid *bacterium*, *Lactobacillus bifidus*, etc.

The antacids include, for example, magnesium carbonate, sodium hydrogen carbonate, magnesium aluminometasilicate, synthetic hydrotalcite, precipitated calcium carbonate, magnesium oxide, etc.

The antiulcer agents include, for example, benzimidazole compounds (e.g. lansoprazole, omeprazole, rabeprazole, pantoprazole), famotidine, cimetidine, ranitidine hydrochloride, etc.

The antitussive-expectorants include, for example, chloperastine hydrochloride, dextromethorphan hydrobromide, theophylline, potassium guaiacolsulfonate, guaifenesin, codeine phosphate, etc.

The antiemetics include, for example, diphenidol hydrochloride, metoclopramide, etc.

The respiratory stimulants include, for example, levallorphan tartrate, etc.

The bronchodilators include, for example, theophylline, salbutamol sulfate, etc.

The antiallergic agents include, for example, amlexanox, seratrodast, etc.

The dental buccal drugs include, for example, oxytetracycline, triamcinolone acetonide, chlorhexidine hydrochloride, lidocaine, etc.

The antihistamines include, for example, diphenhydramine hydrochloride, promethazine, isothipendyl hydrochloride, dl-chlorpheniramine maleate, etc.

The cardiotonics include, for example, caffeine, digoxin, etc.

The antiarryhythmic agents include, for example, procainamide hydrochloride, propranolol hydrochloride, pindolol, etc.

The diuretics include, for example, isosorbide, furosemide, etc.

The hypotensive agents include, for example, delapril hydrochloride, captopril, hexamethonium bromide, hydralazine hydrochloride, labetalol hydrochloride, manidipine hydrochloride, candesartan cilexetil, methyldopa, losartan, valsartan, eprosartan, irbesartan, tasosartan, telmisartan, pomisarutan, ripisartan, forasartan, etc.

The vasoconstrictors include, for example, phenylephrine hydrochloride, etc.

The coronary vasodilators include, for example, carbocromen hydrochloride, molsidomine, verapamil hydrochloride, etc.

The peripheral vasodilators include, for example, cinnarizine, etc.

The antihyperlipidemic agents include, for example, cerivastatin sodium, simvastatin, pravastatin sodium, etc.

The cholagogues include, for example, dehydrocholic acid, trepibutone, etc.

The antibiotics include, for example, cephem antibiotics such as cefalexin, amoxicillin, pivinecillinam hydrochloride, cefotiam dihydrochloride, cefozopran hydrochloride, cefmenoxime hydrochloride, cefsluodin sodium, etc.; synthetic antibacterials such as ampicillin, cyclacillin, sulbenicillin sodium, nalidixic acid, enoxacin. etc.; monobactam antibiotics such as carumonam sodium; penem antibiotics, carbapenem antibiotics, etc.

The chemotherapeutic agents include, for example, sulfamethizole hydrochloride, thiazosulfone, etc.

The agents for treating diabetes include, for example, tolbutamide, voglibose, thiazoline derivatives (e.g. pioglitazone hydrochloride, troglitazone), 5-[[4-[2-(methyl-2-pyridinylamino)ethoxy]phenyl]methyl]-2,4-thiazolidinedione, acarbose, miglitol, emiglitate, etc.

The drugs for osteoporosis include, for example, ipriflavone, etc.

The skeletal muscle relaxants include, for example, methocarbamol, etc.

The antidinics include, for example, meclizine hydrochloride, dimenhydrinate, etc.

The hormones include, for example, riothyroinine sodium, dexamethasone sodium phosphate, prednisolone, oxendolone, leuprorelin acetate, etc.

The alkaloid narcotics include, for example, opium, morphine hydrochloride, ipecac, oxycodone hydrochloride, opium alkaloid hydrochlorides, cocaine hydrochloride, etc.

The sulfadrugs include, for example, sulfanilamide, sufamethizole, etc.

The antipodagrics include, for example, allopurinol, colchicine, etc.

The anticoagulants include, for example, dicoumarol, etc.

The anti-malignant tumor agents include, for example, 5-fluorouracil, uracil, mitomycin, etc.

The agents for Alzheimer's disease include, for example, idebenone, vinpocetine, 8-[1-oxo-3-[1-(phenylmethyl)piperidine-4-yl]propyl]-2,3,4,5-tetrahydro-1H-1-benzazepine or a salt thereof, etc.

The "unstable drug in a polyethylene glycol-containing preparation" is more preferably a compound represented by the formula:

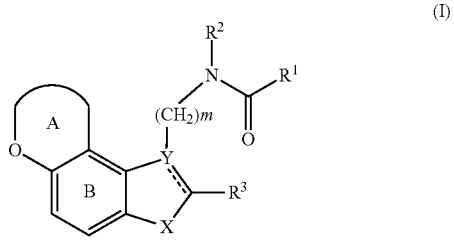

(I)

wherein $R^1$ represents an optionally substituted hydrocarbon group, an optionally substituted amino group or an optionally substituted heterocyclic group,
$R^2$ represents a hydrogen atom or an optionally substituted hydrocarbon group,
$R^3$ represents a hydrogen atom, an optionally substituted hydrocarbon group or an optionally substituted heterocyclic group,
X represents $CHR^4$, $NR^4$, O or S ($R^4$ represents a hydrogen atom or an optionally substitiuted hydrocarbon group),
Y represents C, CH or N (provided that, when X represents $CH_2$, Y is C or CH),
---- represents a single bond or a double bond, ring A represents an optionally substituted 5- to 7-membered heterocyclic ring containing an oxygen atom, ring B represents an optionally substituted benzene ring, and
m represents an integer of 1 to 4, or a salt thereof (hereinafter referred merely to as the compound (I), sometimes).

In the compound (I), $R^1$ represents an optionally substituted hydrocarbon group, an optionally substituted amino group, or an optionally substituted heterocyclic group.

The "hydrocarbon group" of the "optionally substituted hydrocarbon group" represented by $R^1$ include, for example, an aliphatic hydrocarbon group, a monocyclic saturated hydrocarbon group and an aromatic hydrocarbon group, and preferably has 1 to 16 carbon atoms. Specifically, for example, there can be used an alkyl group, an alkenyl group, an alkynyl group, a cycloalkyl group, an aryl group, and the like.

The "alkyl group" is preferably, for example, a lower alkyl group and, for example, there can be generally used a $C_{1-6}$ alkyl group such as ethyl, ethyl, propyl, isopropyl, butyl, isobutyl, sec-butyl and tert-butyl, pentyl, hexyl, etc.

The "alkenyl group" is preferably, for example, a lower alkenyl group and, for example, there can be generally used a $C_{2-6}$ alkenyl group such as vinyl, 1-propenyl, allyl, isopropenyl, butenyl, isobutenyl, etc.

The "alkynyl group" is preferably, for example, a lower alkynyl group and, for example, there can be generally used a $C_{2-6}$ alkynyl group such as ethynyl, propargyl, 1-propenyl, etc.

The "cycloalkyl group" is preferably, for example, a lower cycloalkyl group and, for example, there can be generally used a $C_{3-6}$ cycloalkyl group such as cyclopropyl, cyclobutyl, cyclopentyl, cyclohexyl, etc.

The "aryl group" is preferably, for example, a $C_{6-14}$ aryl group such as phenyl, 1-naphthyl, 2-naphthyl, biphenylyl, 2-anthryl, etc. For example, phenyl group can be generally used.

As the substituent with which the "hydrocarbon group" of the "optionally substituted hydrocarbon group" may be substituted, for example, there can be used a halogen atom (for example, fluorine, chlorine, bromine, iodine, etc.), a nitro group, a cyano group, a hydroxy group, an optionally halogenated lower alkyl group (for example, an optionally halogenated $C_{1-6}$ alkyl group such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, etc.), a lower alkoxy group (for example, a $C_{1-6}$ alkoxy group such as methoxy, ethoxy, propoxy, isopropoxy, butoxy, isobutoxy, pentyloxy, hexyloxy, etc.), an amino group, a mono-lower alkylamino group (for example, a mono-$C_{1-6}$ alkyl amino group such as methylamino, ethylamino, etc.), a di-lower alkylamino group (for example, a di-$C_{1-6}$ alkyl amino group such as dimethylamino, diethylamino, etc.), carboxyl group, a lower alkylcarbonyl group (for example, a $C_{1-6}$ alkylcarbonyl group such as acetyl, propionyl, etc.), a lower alkoxycarbonyl group (for example, a $C_{1-6}$ alkoxy-carbonyl group such as methoxycarbonyl, ethoxycarbonyl, propoxycarbonyl, butoxycarbonyl, etc.), a carbamoyl group, a thiocarbamoyl group, a mono-lower alkylcarbamoyl group (for example, a mono-$C_{1-6}$ alkyl-carbamoyl group such as methylcarbamoyl, ethylcarbamoyl, etc.), a di-lower alkylcarbamoyl group (for example, a di-$C_{1-6}$ alkyl-carbamoyl group such as dimethylcarbamoyl, diethylcarbamoyl, etc.), an arylcarbamoyl group (for example, a $C_{6-10}$ aryl-carbamoyl group such as phenylcarbamoyl, naphthylcarbamoyl, etc.), an aryl group (for example, a $C_{6-10}$ aryl group, etc such as phenyl, naphthyl, etc.), an aryloxy group (for example, a $C_{6-10}$ aryloxy group such as phenyloxy, naphthyloxy, etc.), an optionally halogenated lower alkylcarbonylamino group (for example, an optionally halogenated $C_{1-6}$ alkyl-carbonylamino group such as acetylamino, trifluoroacetylamino, etc.), an oxo group, and the like. The "hydrocarbon group" of the "optionally substituted hydrocarbon group" may have the above-mentioned 1 to 5, preferably 1 to 3 substituents at its substitutable positions and, when the number of the substituents is 2 or more, the respective substituents may be the same or different.

As the preferred "hydrocarbon group" of the "optionally substituted hydrocarbon group" represented by $R^1$, for example, there can be generally used an alkyl group (for example, a $C_{1-6}$ alkyl group such as methyl, ethyl, propyl, isopropyl, etc.), an alkenyl group (for example, a $C_{2-6}$ alkenyl group such as vinyl, etc.), an alkynyl group (for example, a $C_{2-6}$ alkynyl group such as ethynyl, etc.), a cycloalkyl group (for example, a $C_{3-6}$ cycloalkyl group such as cyclopropyl, cyclobutyl, cyclopentyl, cyclohexyl, etc.), an aryl group (for example, a $C_{6-14}$ aryl group such as phenyl, etc.), and the like, particularly an alkyl group (for example, a $C_{1-6}$ alkyl group such as methyl, etc.), a cycloalkyl group (for example, $C_{3-6}$ cyclopropyl such as cyclopropyl, etc.), and the like. The "alkyl group", the "alkenyl group", the "alkynyl group", the "cycloalkyl group" and the "aryl group" may have 1 to 5, and preferably 1 to 3 substituents (preferably, a halogen atom such as fluorine, etc.) with which the above-mentioned "hydrocarbon group" may be substituted.

The "optionally substituted amino group" represented by $R^1$ includes, for example, an amino group which may have the above-mentioned 1 or 2 "optionally substituted hydrocarbon groups", etc., as its substituents. As the preferred substituent with which the "amino group" may be substituted, for example, there can be used 1 or 2 optionally substituted lower alkyl groups or optionally substituted aryl groups, etc., particularly, one optionally substituted lower alkyl group is used. As the "lower alkyl group", for example, there can be used a $C_{1-6}$ alkyl group such as methyl, ethyl, propyl, isopropyl, butyl, isobutyl, sec-butyl, tert-butyl, etc. The "lower alkyl group" may have 1 to 3 substituents with which the above-mentioned "hydrocarbon group" may be substituted. As the "aryl group", for example, there can be used a $C_{6-10}$ aryl group such as phenyl group, etc. The "aryl group" may have 1 to 5, preferably 1 to 3 substituents with which the above-mentioned "hydrocarbon group" may be substituted (preferably a halogen atom such as fluorine, chlorine, etc., and a $C_{1-6}$ alkoxy group such as methoxy, ethoxy, etc.). As the "optionally substituted amino group", for example, there can be generally used a phenylamino group substituted with 1 to 3 lower alkoxy groups (for example, a $C_{1-4}$ alkoxy group such as methoxy, etc.), a monoalkylamino group substituted with a lower alkyl group (for example, a $C_{1-4}$ alkyl group such as methyl, ethyl, propyl, butyl, tert-butyl, etc.), and the like.

The "heterocyclic group" of the "optionally substituted heterocyclic group" represented by $R^1$ includes, for example, a 5- to 14-membered (preferably 5- to 10-membered) (monocyclic to tricyclic, and preferably monocyclic or dicyclic) heterocyclic group containing one or two kinds of 1 to 4 (preferably 1 to 3) hetero atoms selected from a nitrogen atom, an oxygen atom and a sulfur atom, in addition to carbon atoms, and the like. For example, there can be used, for example, a 5-membered ring group containing 1 to 4 hetero atoms selected from an oxygen atom, a sulfur atom and a nitrogen atom, in addition to carbon atoms, such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl, 1H- or 2H-tetrazolyl, etc.; a 6-membered ring group containing 1 to 4 hetero atoms selected from an oxygen atom, a sulfur atom and a nitrogen atom, in addition to carbon atoms, such as 2-, 3- or 4-pyridyl, N-oxide-2-, 3- or 4-pyridyl, 2-, 4- or 5-pyrimidinyl, N-oxide-2-, 4- or 5-pyrimidinyl, thiomorpholinyl, morpholinyl, piperidino, 2-, 3- or 4-piperidyl, thiopyranyl, 1,4-oxadinyl, 1,4-thiadinyl, 1,3-thiadinyl, piperadinyl, triazinyl, 3- or 4-pyridazinyl, pyrazinyl, N-oxide-3- or 4-pyridazinyl, etc.; a dicyclic or tricyclic condensed ring group containing 1 to 4 hetero atoms selected from an oxygen atom, a sulfur atom and a nitrogen atom, in addition to carbon atoms (preferably a group formed by condensing the above-mentioned 5- to 6-membered ring group with one or two 5 to 6-membered ring groups optionally containing 1 to 4 hetero atoms selected from an oxygen atom, a sulfur atom and a nitrogen atom, in addition to carbon atoms) such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolidinyl, 1,8-naphthylidinyl, dibenzofuranyl, carbazolyl, acrydinyl, phenanthridinyl, chromanyl, phenothiazinyl, phenoxazinyl, etc.; and the like. Among these, preferred is a 5- or 7-membered (preferably 5- or 6-membered) heterocyclic group containing 1 to 3 hetero atoms selected from oxygen atom, sulfur atom and nitrogen atom, in addition to carbon atoms.

As preferred "heterocyclic group" of the "optionally substituted heterocyclic group" represented by $R^1$, for example, there can be used a 5- or 6-membered heterocyclic group containing 1 to 3 hetero atoms selected from an oxygen atom, a sulfur atom and a nitrogen atom, in addition to carbon atoms, and the like. Specific examples thereof include 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2-furyl or 3-furyl, pyrazinyl, 2-pyrimidinyl, 3-pyrrolyl, 3-pyridazinyl, 3-isothiazolyl, 3-isooxazolyl, etc. Among these, particularly preferably, a 6-membered nitrogen-containing heterocyclic group (for example, pyridyl, etc.), and the like are used.

As the substituent with which "heterocyclic group" of the "optionally substituted heterocyclic group" may be substituted, for example, there can be used a halogen atom (for example, fluorine, chlorine, bromine, iodine, etc.), a lower alkyl group (for example, a $C_{1-6}$ alkyl group such as methyl, ethyl, propyl, isopropyl, butyl, isobutyl, sec-butyl, tert-butyl, pentyl, hexyl, etc.), a cycloalkyl group (for example, a $C_{3-6}$ cycloalkyl group such as cyclopropyl, cyclobutyl, cyclopentyl, cyclohexyl, etc.), a lower alkynyl group (for example, a $C_{2-6}$ alkynyl group such as ethynyl, 1-propenyl, propargyl, etc.), a lower alkenyl group (for example, a $C_{2-6}$ alkenyl group such as vinyl, allyl, isopropenyl, butenyl, isobutenyl, etc.), an aralkyl group (for example, a $C_{7-11}$ aralkyl group such as benzyl, α-methylbenzyl, phenethyl, etc.), an aryl group (for example, a $C_{6-10}$ aryl group such as phenyl, naphthyl, etc., and preferably a phenyl group, etc.), a lower alkoxy group (for example, a $C_{1-6}$ alkoxy group such as methoxy, ethoxy, propoxy, isopropoxy, butoxy, isobutoxy, sec-butoxy, tert-butoxy, etc.), an aryloxy group (for example, $C_{6-10}$ aryloxy group such as phenoxy, etc.), a lower alkanoyl group (for example, a $C_{1-6}$ alkyl-carbonyl group such as formyl, acetyl, propionyl, butyryl, isobutyryl, etc.), an arylcarbonyl (for example, a $C_{6-10}$ aryl-carbonyl group such as benzoyl group, naphthoyl group, etc.), a lower alkanoyloxy group (for example, a $C_{1-6}$ alkyl-carbonyloxy group such as formyloxy, acetyloxy, propionyloxy, butyryloxy, isobutyryloxy, etc.), an arylcarbonyloxy group (for example, a $C_{6-10}$ aryl-carbonyloxy group such as benzoyloxy, naphthoyloxy, etc.), a carboxyl group, a lower alkoxycarbonyl group (for example, a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl, etc.), aralkyloxycarbonyl (for example, a $C_{7-11}$ aralkyloxycarbonyl group such as benzyloxycarbonyl, etc.), a carbamoyl group, a mono-, di- or tri-halogeno-lower alkyl group (for example, a mono-, di- or tri-halogeno-$C_{1-4}$ alkyl group such as chloromethyl, dichloromethyl, trifluoromethyl, 2,2,2-trifluoroethyl, etc.), an oxo group, an amidino group, an imino group, an amino group, a mono-lower alkylamino group (for example, a mono-$C_{1-4}$ alkylamino group such as methylamino, ethylamino, propylamino, isopropylamino, butylamino, etc.), a di-lower alkylamino group (for example, a di-$C_{1-4}$ alkylamino group such as dimethylamino, diethylamino, dipropylamino, diisopropylamino, dibutylamino, methylethylamino, etc.), a 3- to 6-membered cyclic amino group which may contain 1 to 3 hetero atoms selected from an oxygen atom, a sulfur atom and a nitrogen atom, in addition to carbon atoms and one nitrogen atom (for example, a 3- to 6-membered cyclic amino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, N-ethylpiperazinyl, etc.), an alkylenedioxy group (for example, a $C_{1-3}$ alkylenedioxy group such as methylenedioxy, ethylenedioxy, etc.), a hydroxy group, a nitro group, a cyano group, a mercapto group, a sulfo group, a sulfino group, a phosphono group, a sulfamoyl group, a monoalkylsulfamoyl group (for example, a mono-$C_{1-6}$ alkyl-sulfamoyl group such as N-methylsulfamoyl, N-ethylsulfamoyl, N-propylsulfamoyl, N-isopropylsulfamoyl, N-butylsulfamoyl, etc.), a dialkylsulfamoyl group (for example, a di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (for example, a $C_{1-6}$ alkylthio group such as methylthio, ethylthio, propylthio, isopropylthio, butylthio, sec-butylthio, tert-butylthio, etc.), an arylthio group (for example, a $C_{6-10}$ arylthio group such as phenylthio, naphthylthio, etc.), a lower alkylsulfinyl group (for example, a $C_{1-6}$ alkylsulfinyl group such as methylsulfinyl, ethylsulfinyl, propylsulfinyl, butylsulfinyl, etc.), an arylsulfinyl group (for example, a $C_{6-10}$ arylsulfinyl group such as phenylsulfinyl, naphthylsulfinyl, etc.), a lower alkylsulfonyl group (for example, a $C_{1-6}$ alkylsulfonyl group such as methylsulfonyl, ethylsulfonyl, propylsulfonyl, butylsulfonyl, etc.), an arylsulfonyl group (for example, a $C_{6-10}$ arylsulfonyl group such as phenylsulfonyl, naphthylsulfonyl, etc.), and the like.

The "heterocyclic group" of the "optionally substituted heterocyclic group" may have the above-mentioned 1 to 5, and preferably 1 to 3 substituents at its substitutable positions and, when the number of substituents is 2 or more, the respective substituents may be the same or different.

As preferred substituent of the "optionally substituted heterocyclic group" represented by $R^1$, for example, there can be used a halogen atom (for example, chlorine, fluorine, etc.), a $C_{1-6}$ alkyl group (for example, methyl, ethyl, etc.), a $C_{1-6}$ alkoxy group (for example, methoxy, ethoxy, etc.), an aralkyloxycarbonyl group (for example, a $C_{7-12}$ aralkyloxycarbonyl such as benzyloxycarbonyl, etc.), and the like.

$R^1$ is preferably, for example, (i) an optionally substituted lower alkyl group, (ii) an optionally substituted lower cycloalkyl group, (iii) an optionally substituted lower alkenyl group, (iv) an optionally substituted aryl group, (v) an optionally substituted mono- or di-lower alkylamino group, (vi) an optionally substituted arylamino group, vii) an optionally substituted 5- or 6-membered nitrogen-containing heterocyclic group, or the like.

The above-mentioned "lower alkyl group" is preferably, for example, a $C_{1-6}$ alkyl group such as methyl, ethyl, propyl, isopropyl, butyl, pentyl, hexyl, etc. The "lower cycloalkyl group" is preferably, for example, a $C_{3-5}$ cycloalkyl group such as cyclopropyl, cyclobutyl, cyclopentyl, cyclohexyl, etc. The "lower alkenyl group" is preferablty, for example, a $C_{2-6}$ alkenyl group such as vinyl, 1-propenyl, butenyl, etc. The "aryl group" is preferably, for example, a $C_{6-10}$ aryl group such as phenyl, 1-naphthyl, 2-naphthyl, etc. The "lower alkylamino group" is preferably, for example, a mono- or di-$C_{1-6}$ alkyl amino group such as methylamino, ethylamino, propylamino, isopropylamino, butylamino, tert-butylamino, dimethylamino, diethylamino, methylethylamino, etc. The "arylamino group" is preferably, for example, a $C_{6-10}$ arylamino group such as phenylamino, etc. The "5- or 6-membered nitrogen-containing heterocyclic group" is preferably, for example, a 5- or 6-membered nitrogen-containing heterocyclic group such as 2-, 3- or 4-pyridyl, etc. As the substituent with which these groups may be substituted, for example, there can be used 1 to 5 substituens, with which the above-mentioned "hydrocarbon group" may be substituted.

More preferred examples of $R^1$ include (i) a $C_{1-6}$ alkyl group which may be substituted with 1 to 4 halogens or $C_{1-6}$ alkoxy groups, (ii) a $C_{3-6}$ cycloalkyl group, (iii) a $C_{2-6}$ alkenyl group, (iv) a $C_{6-10}$ aryl group which may be substituted with 1 to 4 $C_{1-6}$ alkoxy groups, nitro groups, halogeno $C_{1-6}$ alkyl-carbonylamino groups or halogen atoms, (v) a mono- or di-$C_{1-6}$ alkyl amino group, (vi) a $C_{6-10}$ arylamino group which may be substituted with 1 to 3 $C_{1-6}$ alkoxy groups, (vii) a 6-membered nitrogen-containing heterocyclic group which may be substituted with 1 to 2 $C_{7-11}$ aralkyloxycarbonyl groups, and the like. Particularly, there can be generally used an optionally halogenated $C_{1-6}$ alkyl group (for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, etc.), a $C_{3-6}$ cycloalkyl group (for example, cyclopropyl, cyclobutyl, cyclopentyl, cyclohexyl, etc.), a mono-$C_{1-6}$ alkyl amino group (for example, methylamino, ethylamino, propylamino, isopropylamino, butylamino, tert-butylamino, etc.), and the like. Among these, an optionally halogenated $C_{1-6}$ alkyl group or a mono-$C_{1-6}$ alkyl amino group is preferably, with an optionally halogenated $C_{1-6}$ alkyl group, and particularly a $C_{1-3}$ alkyl group (for example, methyl, ethyl, propyl, etc.) being more preferred.

$R^2$ in the compound (I) represents a hydrogen atom or an optionally substituted hydrocarbon group.

As $R^2$, a hydrogen atom or optionally substituted lower ($C_{1-6}$) alkyl group is preferably used, more preferably a hydrogen atom or a lower ($C_{1-6}$) alkyl group, with a hydrogen atom being particularly preferably used. The "substituent" of the "optionally substituted lower ($C_{1-6}$) alkyl group"

include, for example, the substituent with which the above-mentioned "hydrocarbon group" may be substituted.

$R^3$ in the compound (I) represents a hydrogen atom, an optionally substituted hydrocarbon group or an optionally substituted heterocyclic group.

As the preferred "hydrocarbon group" of the "optionally substituted hydrocarbon group" represented by $R^3$, for example, there can be generally used an alkyl group (for example, a $C_{1-6}$ alkyl group such as methyl, ethyl, propyl, isopropyl, etc.), an alkenyl group (for example, a $C_{2-6}$ alkenyl group such as vinyl, etc.), an alkynyl group (for example, a $C_{2-6}$ alkynyl group such as ethynyl, etc.), a cycloalkyl group (for example, a $C_{3-6}$ cycloalkyl group such as cyclopropyl, cyclobutyl, cyclopentyl, cyclohexyl, etc.), an aryl group (for example, a $C_{6-14}$ aryl group such as phenyl, etc.), and the like, and particularly an alkyl group (for example, a $C_{1-6}$ alkyl group such as methyl, etc.), an aryl group (for example, a $C_{6-14}$ aryl group such as phenyl, etc.), and the like. The "alkyl group", the "alkenyl group", the "alkynyl group", the "cycloalkyl group" and the "aryl group" may have 1 to 5, and preferably 1 to 3 substituents (preferably, a halogen atom such as fluorine, etc.) with which the above-mentioned "hydrocarbon group" may be substituted, and the like.

As the preferred "heterocyclic group" of the "optionally substituted heterocyclic group" represented by $R^3$, for example, there can be used a 5- or 6-membered heterocyclic group containing 1 to 3 hetero atoms selected from a nitrogen atom, an oxygen atom and a sulfur atom, in addition to carbon atoms, and the like. Specific examples thereof include 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isooxazolyl, and the like. Among these, particularly preferably, a 6-membered nitrogen-containing heterocyclic group (for example, pyridyl, etc.) is used.

As the preferred substituent of the "optionally substituted heterocyclic group" represented by $R^3$ for example, there can be used a halogen atom (for example, chlorine, fluorine, etc.), a $C_{1-6}$ alkyl group (for example, methyl, ethyl, etc.), a $C_{1-6}$ alkoxy group (for example, methoxy, ethoxy, etc.), an aralkyloxycarbonyl group (for example, a $C_{7-12}$ aralkyloxycarbonyl such as benzyloxycarbonyl, etc.), an amino group, a mono-$C_{1-6}$ alkyl amino group (for example, methylamino, ethylamino, etc.), a di-$C_{1-6}$ alkyl amino group (for example, dimethylamino, diethylamino, etc.), and the like.

$R^3$ is preferably, for example, (i) a hydrogen atom, (ii) an optionally substituted lower alkyl group, (iii) an optionally substituted aryl group, (iv) an optionally substituted 5- or 6-membered heterocyclic group, and the like, and more preferably (i) a hydrogen atom, (ii) a lower alkyl group, (iii) an optionally substituted $C_{6-10}$ aryl group, (iv) an optionally substituted 6-membered nitrogen-containing heterocyclic group, and the like. Examples of the substituent include a halogen atom, a $C_{1-6}$ alkyl group, a $C_{1-6}$ alkoxy group, an amino group, a mono-$C_{1-6}$ alkyl amino group, a di-$C_{1-6}$ alkyl amino group, and the like. More preferably, $R^3$ is a hydrogen atom, a phenyl group or a 2-, 3- or 4-pyridyl group. A hydrogen atom is particularly preferred.

X in the compound (I) represents $CHR^4$, $NR^4$, O or S ($R^4$ represets a hydrogen atom or an optionally substituted hydrocarbon group).

As $R^4$, a hydrogen atom or an optionally substituted lower ($C_{1-6}$) alkyl group is preferred and a hydrogen atom is generally used.

X is preferably $CHR^4$ ($R^4$ is as defined above), O or S. Alternatively, X is preferably $CHR^4$ or $NR^4$ ($R^4$ is as defined above).

Y in the compound (I) represents C, CH or N. C or CH is preferred.

The ring A in the compound (I) represents an optionally substituted 5- to 7-membered heterocyclic ring containing an oxygen atom.

Examples of the "5- or 7-membered heterocyclic ring containing an oxygen atom" include a 5- or 7-membered (preferably 5- or 6-membered) heterocyclic ring which may contain one or two kinds of 1 to 3 (preferably 1 or 2) selected from a nitrogen atom, an oxygen atom and a sulfur atom, in addition to carbon atoms and the oxygen atom. As the ring, preferred is a ring represented by the formula:

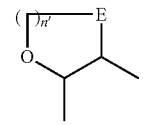

wherein E represents (i) $CH_2CH_2$, (ii) CH=CH, (iii) $CH_2O$, (iv) $OCH_2$, (v) $CH_2S(O)q'$ (q' represents an integer of 0 to 2), (vi) $S(O)q'CH_2$ (q' is as defined above), (vii) $CH_2NH$, (viii) $NHCH_2$, (ix) N=N, (x) CH=N, (xi) N=CH or (xii) CONH, and n' represents an integer of 0 to 2.

E is preferably (i) $CH_2CH_2$, (ii) CH=CH, (iii) $CH_2O$, (iv) $OCH_2$, (v) $CH_2NH$, (vi) $NHCH_2$, (vii) N=N, (viii) CH=N or (ix) N=CH, and particularly preferably (i) $CH_2CH_2$ or (ii) CH=CH.

Specifically, for example, preferred are a 5-membered heterocyclic ring having an oxygen atom, such as 2,3-dihydrofuran, furan, 1,3-dioxazole, oxazoline, isoxazole, 1,2,3-oxadiazole, oxazole, etc., a 6-membered heterocyclic ring having an oxygen atom, such as 2H-3,4-dihydropyran, 2H-pyran, 2,3-dehydro-1,4-dioxane, 2,3-dehydromorpholine, etc., and the like.

More preferred is a ring represented by the formula:

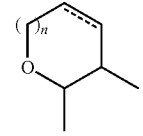

wherein n represents an integer of 0 to 2, and ---- represents a single bond or a double bond.

Specifically, for example, 2,3-dihydrofuran, furan, 2H-3,4-dihydropyran and 2H-pyran are generally used.

As the substituent on the ring A, for example, there can be used a halogen atom (for example, fluorine, chlorine, bromine, iodine, etc.), an optionally substituted lower alkyl group, an optionally substituted cycloalkyl group, an optionally substituted lower alkynyl group, an optionally substituted lower alkenyl group, an optionally substituted aryl group, a lower alkoxy group (for example, a $C_{1-6}$ alkoxy group such as methoxy, ethoxy, propoxy, isopropoxy, butoxy, isobutoxy, sec-butoxy, tert-butoxy, etc.), an aryloxy group (for example, a $C_{6-10}$ aryloxy group such as phenoxy, etc.), a lower alkanoyl group (for example, a $C_{1-6}$ alkyl-carbonyl group such as formyl, acetyl, propionyl, butyryl, isobutyryl, etc.), an arylcarbonyl group (for example, a $C_{6-10}$ aryl-carbonyl group such as benzoyl group, naphthoyl group, etc.), a lower alkanoyloxy group (for example, a $C_{1-6}$ alkyl-carbonyloxy group such as formyloxy, acetyloxy, propionyloxy, butyryloxy, isobutyryloxy, etc.), an arylcarbonyloxy group (for example, a $C_{6-10}$ aryl-carbonyloxy group such as benzoyloxy, naphthoyloxy, etc.), a carboxyl group, a lower alkoxycarbonyl group (for example, a $C_{1-6}$ alkoxycarbonyl group such as methoxycarbonyl, ethoxycarbonyl, propoxycarbonyl, isopropoxycarbonyl, butoxycarbonyl, isobutoxycarbonyl, tert-butoxycarbonyl, etc.), an aralkyloxycarbonyl (for example, a $C_{7-11}$ aralkyloxy-carbonyl group such as benzyloxycarbonyl, etc.), a carbamoyl group, a thiocarbamoyl group, a mono-, di- or tri-halogeno-lower alkyl group (for example, a mono-, di- or tri-halogeno-$C_{1-4}$ alkyl group such as chloromethyl, dichloromethyl, trifluoromethyl, 2,2,2-trifluoroethyl, etc.), an oxo group, an amidino group, an imino group, an amino group, a mono-lower alkylamino group (for example, a mono-$C_{1-4}$ alkylamino group such as methylamino, ethylamino, propylamino, isopropylamino, butylamino, etc.), a di-lower alkylamino group (for example, a di-$C_{1-4}$ alkylamino group such as dimethylamino, diethylamino, dipropylamino, diisopropylamino, dibutylamino, methylethylamino, etc.), a 3-to 6-membered cyclic amino group which may have 1 to 3 hetero atoms selected from an oxygen atom, a sulfur atom and a nitrogen atom, in addition to carbon atoms and one nitrogen atom (for example, a 3- to 6-membered cyclic amino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, N-ethylpiperazinyl, etc.), an alkylenedioxy group (for example, a $C_{1-3}$ alkylenedioxy group such as methylenedioxy, ethylenedioxy, etc.), a hydroxy group, a nitro group, a cyano group, a mercapto group, a sulfo group, a sulfino group, a phosphono group, a sulfamoyl group, a monoalkylsulfamoyl group (for example, a mono-$C_{1-6}$ alkylsulfamoyl group such as N-methylsulfamoyl, N-ethylsulfamoyl, N-propylsulfamoyl, N-isopropylsulfamoyl, N-butylsulfamoyl, etc.), a dialkylsulfamoyl group (for example, a di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (for example, a $C_{1-6}$ alkylthio group such as methylthio, ethylthio, propylthio, isopropylthio, butylthio, sec-butylthio, tert-butylthio, etc.), an arylthio group (for example, a $C_{6-10}$ arylthio group such as phenylthio, naphthylthio, etc.), a lower alkylsulfinyl group (for example, $C_{1-6}$ alkylsulfinyl group such as methylsulfinyl, ethylsulfinyl, propylsulfinyl, butylsulfinyl, etc.), an arylsulfinyl group (for example, a $C_{6-10}$ arylsulfinyl group such as phenylsulfinyl, naphthylsulfinyl, etc.), a lower alkylsulfonyl group (for example, a $C_{1-6}$ alkylsulfonyl group such as methylsulfonyl, ethylsulfonyl, propylsulfonyl, butylsulfonyl, etc.), an arylsulfonyl group (for example, a $C_{6-10}$ arylsulfonyl group such as phenylsulfonyl, naphthylsulfonyl, etc.) and the like.

The "lower alkyl group", the "lower alkenyl group", the "lower alkynyl group", the "lower cycloalkyl group" and the "aryl group" may have 1 to 5, and preferably 1 to 3 substituents with which the above-mentioned "hydrocarbon group" may be substituted.

Preferred examples of the substituent of the ring A include a halogen atom, an optionally substituted $C_{1-6}$ alkyl group, an optionally substituted $C_{1-6}$ alkoxy group, a hydroxy group, a nitro group, a cyano group, an optionally substituted amino group, an oxo group, and the like. The "substituent" of the "optionally substituted $C_{1-6}$ alkyl group", the "optionally substituted $C_{1-6}$ alkoxy group" and the "optionally substituted amino group" is, for example, a substituent with which the above-mentioned "hydrocarbon group" may be substituted.

The ring A may have the above-mentioned 1 to 4, and preferably 1 to 2 substituents at its substitutable positions according to the size of a ring and, when the number of substituents is 2 or more, the respective substituents may be the same or different.

The ring A includes, for example, that represented by:

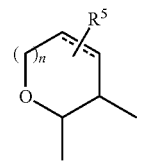

wherein n is as defined above, and $R^5$ represents a hydrogen atom or 1 or 2 substituents represented by the above-mentioned "preferred substituent of the ring A", and the like. Among these, those wherein $R^5$ is a hydrogen atom or an optionally substituted $C_{1-6}$ alkyl group, particularly those wherein $R^5$ is a hydrogen atom (unsubstituted ring A) are generally used.

The ring B in the compound (I) represents an optionally substituted benzene ring.

The substituent of the ring B includes, for example, substituents of the above-mentioned "optionally substituted benzene ring". Among these, a halogen atom or an optionally substituted lower ($C_{1-6}$) alkyl group is preferred, and particularly a halogen atom or a lower ($C_{1-6}$) alkyl group (preferably, methyl) is generally used. The "substituent" of the "optionally substituted lower ($C_{1-6}$) alkyl group" is, for example, a substituent with which the above-mentioned "hydrocarbon group" may be substituted.

The ring B may have 1 or 2, and preferably 1 substituents at its substitutable positions and, when the number of substituents is 2, the respective substituents may be the same or different.

The ring B is preferably, for example, that represented by:

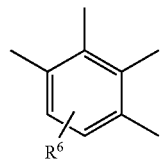

wherein $R^6$ represents a hydrogen atom, a halogen atom, an optionally substituted lower ($C_{1-6}$) alkyl group or an optionally substituted lower ($C_{1-6}$) alkoxy group, and the like. $R^6$ is prefearbly, for example, a hydrogen atom, a halogen atom or a lower ($C_{1-6}$) alkyl group (preferably, methyl). A hydrogen atom is more preferred.

m in the compound (I) represents an integer of 1 to 4. m is preferably an integer of 1 to 3. Furthermore, m is preferably 2 or 3. Particularly preferably, m is 2.

In the above formula, n represents an integer of 0 to 2. n is preferably an integer of 0 or 1.

Particularly preferably, n is 0.

Examples of

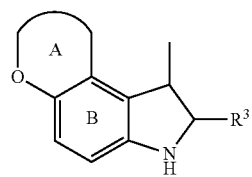 include

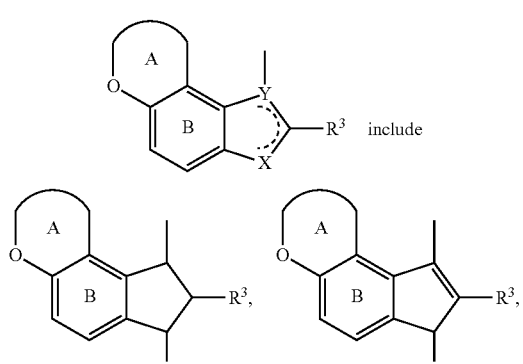

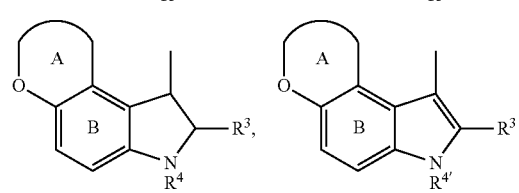

wherein $R^{4'}$ represents an optionally substituted hydrocarbon group and the other symbols are as defined above, and the like.

$R^{4'}$ is preferably an optionally substituted lower ($C_{1-3}$) alkyl.

Preferred examples of

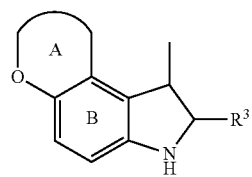 include

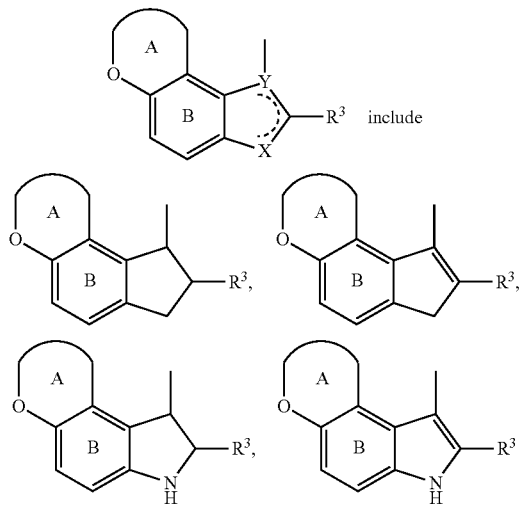

wherein the respective symbols are as defined above, and the like. Among these, preferred are

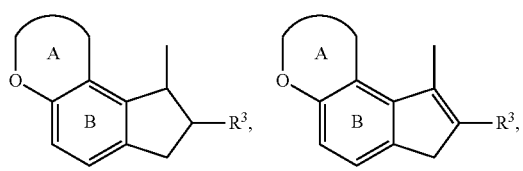

-continued

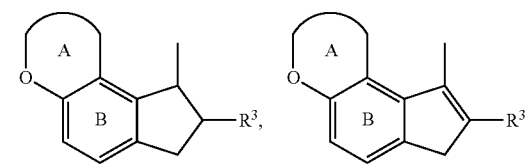

wherein the respective symbols are as defined above, and the like.

In addition, (i)

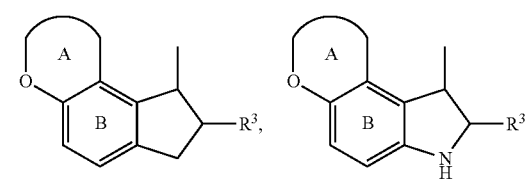

(ii)

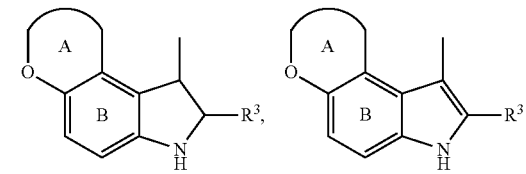

or (iii)

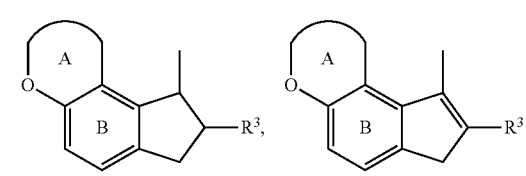

wherein the respective symbols are as defined above, and the like are preferably used.

Among these,

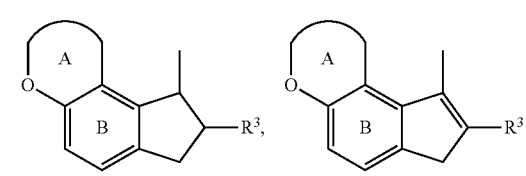

wherein the respective symbols are as defined above, and the like are preferred. Particularly preferred is

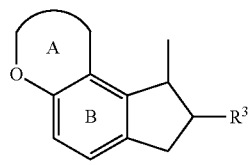

wherein the respective symbols are as defined above.

As the compound (I), for example, those having the following structural formulas, and the like are generally and particularly used:

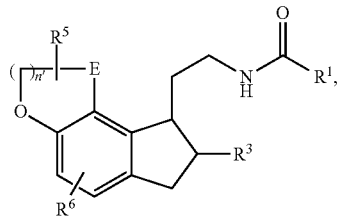

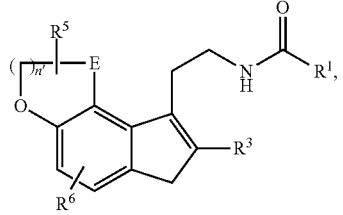

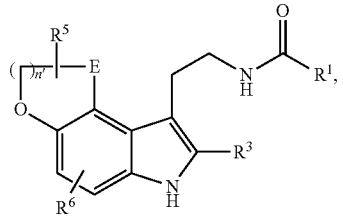

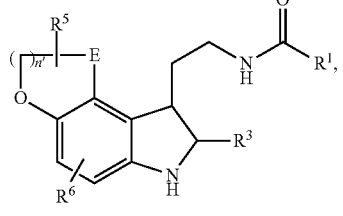

wherein the respective symbols are as defined above.

Preferred examples of the compound (I) include compound represented by the following formulas:

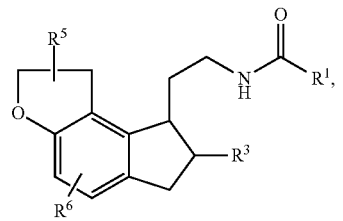

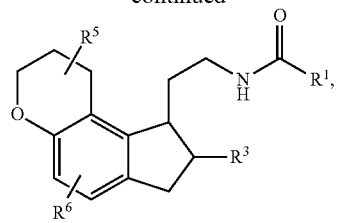

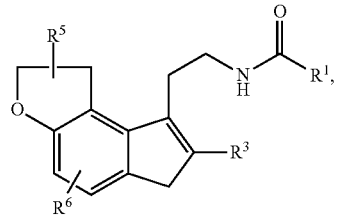

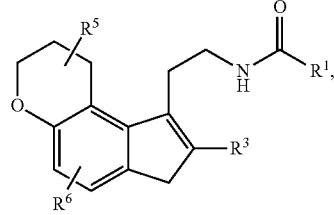

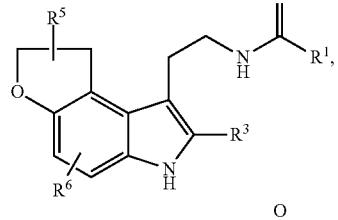

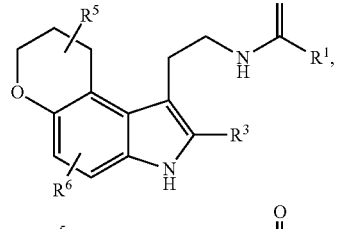

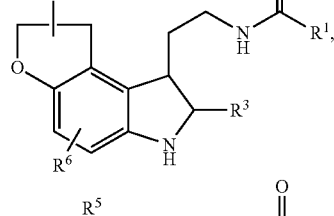

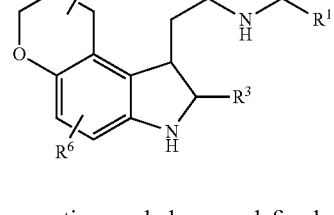

wherein the respective symbols are as defined above, and the like.

Preferred examples of the compound (I) also include compounds wherein $R^1$ represents (i) an optionally substituted lower alkyl group, (ii) an optionally substituted lower cycloalkyl group, (iii) an optionally substituted lower alkenyl group, (iv) an optionally substituted aryl group, (v) an optionally substituted mono- or di-lower alkylamino group, (vi) an optionally substituted arylamino group or (vii) an optionally substituted 5- or 6-membered nitrogen-containing heterocyclic group, R² represents a hydrogen atom or an optionally substituted lower ($C_{1-6}$) alkyl group, R³ represents (i) a hydrogen atom, (ii) an optionally substituted lower alkyl group or (iii) an optionally substituted aryl group, X represents CHR⁴ or NR⁴ (R⁴ represents a hydrogen atom or a lower ($C_{1-6}$) alkyl group which may be substituted with an oxo group), Y represents C, CH or N (provided that, when X represents $CH_2$, Y is C or CH), ---- represents a single bond or a double bond, ring A represents an optionally substituted 5- to 7-membered heterocyclic ring containing an oxygen atom, ring B represents an optionally substituted benzene ring, and m represents 1 or 2.

More preferred is a compound wherein R¹ represents (i) a $C_{1-6}$ alkyl group which may be substituted with 1 to 4 halogens or $C_{1-6}$ alkoxy groups, (ii) a $C_{3-6}$ cycloalkyl group, (iii) a $C_{2-6}$ alkenyl group, (iv) a $C_{6-10}$ aryl group which may be substituted with 1 to 4 $C_{1-6}$ alkoxy groups, nitro groups, halogeno $C_{1-6}$ alkyl-carbonylamino groups or halogen atoms, (v) a mono- or di-$C_{1-6}$ alkylamino group, (vi) a $C_{6-10}$ arylamino group which may be 1 to 3 $C_{1-6}$ alkoxy groups or (vii) a 6-membered nitrogen-containing heterocyclic group which may be 1 to 2 $C_{7-11}$ aralkyloxy-carbonyl groups, R² represents a hydrogen atom or lower ($C_{1-6}$) alkyl group, R³ represents (i) a hydrogen atom, (ii) a lower ($C_{1-6}$) alkyl group or (iii) a $C_{6-14}$ aryl group, X represents CHR⁴ or NR⁴ (R⁴ represents a lower ($C_{1-6}$) alkyl group which may be substituted with a hydrogen atom or an oxo group), Y represents C, CH or N (provided that, when X represents $CH_2$, Y is C or CH), ---- represents a single bond or a double bond, ring A represents the following:

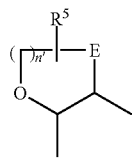

wherein the respective symbols are as defined above, ring B represents the following:

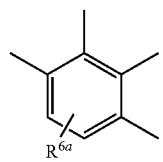

wherein R⁶a represents a hydrogen atom, a halogen atom or a lower ($C_{1-6}$) alkyl group, and m represents 1 or 2, and the like.

Among these, a compound represented by the formula:

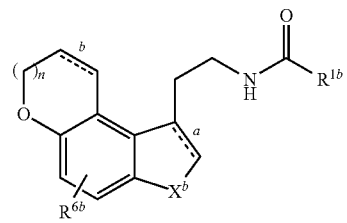

and a compound represented by the formula:

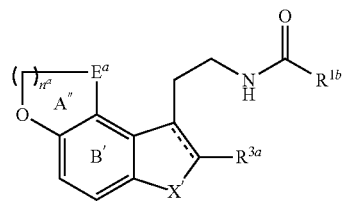

Preferred examples of the compound (I) include:
N-[2-(1,6,7,8-tetrahydro-2H-indeno[5,4-b]furan-8-yl)ethyl] acetamide,
N-[2-(1,6,7,8-tetrahydro-2H-indeno[5,4-b]furan-8-yl)ethyl] butylamide,
N-[2-(1,6,7,8-tetrahydro-2H-indeno[5,4-b]furan-8-yl)ethyl] propionamide,
N-[2-(3,7,8,9-tetrahydropyrano[3,2-e]indol-1-yl)ethyl]propionamide,
N-[2-(5-fluoro-3,7,8,9-tetrahydrocyclopenta[f][1]benzopyran-9-yl)ethyl]propionamide,
N-[2-(3,7,8,9-tetrahydropyrano[3,2-e]indol-1-yl)ethyl]butylamide,
N-[2-(1,2,3,7,8,9-hexahydropyrano[3,2-e]indol-1-yl)ethyl] propionamide,
N-[2-(1,2,3,7,8,9-hexahydropyrano[3,2-e]indol-1-yl)ethyl] butylamide,
N-[2-(4-fluoro-1,6,7,8-tetrahydro-2H-indeno[5,4-b]furan-8-yl)ethyl]butylamide,
N-[2-(4-fluoro-1,6,7,8-tetrahydro-2H-indeno[5,4-b]furan-8-yl)ethyl]propionamide,
(S)—N-[2-(1,6,7,8-tetrahydro-2H-indeno[5,4-b]furan-8-yl) ethyl]propionamide,
(R)—N-[2-(1,6,7,8-tetrahydro-2H-indeno[5,4-b]furan-8-yl) ethyl]propionamide,
N-[2-(1,6,7,8-tetrahydro-2H-indeno[5,4-b]furan-8-yl)ethyl] butylamide,
N-[2-(1,6-dihydro-2H-indeno[5,4-b]furan-8-yl)ethyl]acetamide,
N-[2-(1,6-dihydro-2H-indeno[5,4-b]furan-8-yl)ethyl]propionamide,
N-[2-(1,6-dihydro-2H-indeno[5,4-b]furan-8-yl)ethyl]butylamide,
N-[2-(7,8-dihydro-6H-indeno[4,5-d]-1,3-dioxazole-8-yl) ethyl]propionamide,
N-[2-(7,8-dihydro-6H-indeno[4,5-d]-1,3-dioxazole-8-yl) ethyl]butylamide,
N-[2-(2,3,8,9-tetrahydro-7H-indeno[4,5-b]-1,4-dioxyn-9-yl)ethyl]propionamide,
N-[2-(2,3,8,9-tetrahydro-7H-indeno[4,5-b]-1,4-dioxyn-9-yl)ethyl]butylamide, N-[2-(1,6,7,8-tetrahydro-2H-furo[3,2-e]indol-8-yl)ethyl]
propionamide,
N-[2-(1,6,7,8-tetrahydro-2H-furo[3,2-e]indol-8-yl)ethyl]bu-
tylamide,
N-[2-(7-phenyl-1,6-dihydro-2H-indeno[5,4-b]furan-8-yl)
ethyl]propionamide, and
N-[2-(7-phenyl-1,6-dihydro-2H-indeno[5,4-b]furan-8-yl)
ethyl]butylamide.
More preferred examples thereof include:
N-[2-(1,6,7,8-tetrahydro-2H-indeno[5,4-b]furan-8-yl)ethyl]
acetamide,
N-[2-(1,6,7,8-tetrahydro-2H-indeno[5,4-b]furan-8-yl)ethyl]
propionamide,
N-[2-(5-fluoro-3,7,8,9-tetrahydrocyclopenta[f][1]benzopy-
ran-9-yl)ethyl]propionamide,
N-[2-(5-fluoro-1,2,3,7,8,9-hexahydrocyclopenta[f][1]ben-
zopyran-9-yl)ethyl]propionamide,
(S)—N-[2-(1,6,7,8-tetrahydro-2H-indeno[5,4-b]furan-8-yl)
ethyl]propionamide,
(R)—N-[2-(1,6,7,8-tetrahydro-2H-indeno[5,4-b]furan-8-yl)
ethyl]propionamide,
N-[2-(1,6,7,8-tetrahydro-2H-indeno[5,4-b]furan-8-yl)ethyl]
butylamide,
N-[2-(1,6-dihydro-2H-indeno[5,4-b]furan-8-yl)ethyl]acet-
amide,
N-[2-(1,6-dihydro-2H-indeno[5,4-b]furan-8-yl)ethyl]pro-
pionamide,
N-[2-(1,6-dihydro-2H-indeno[5,4-b]furan-8-yl)ethyl]butyl-
amide,
N-[2-(1,6,7,8-tetrahydro-2H-furo[3,2-e]indol-8-yl)ethyl]
propionamide,
N-[2-(1,6,7,8-tetrahydro-2H-furo[3,2-e]indol-8-yl)ethyl]bu-
tylamide,
N-[2-(7-phenyl-1,6-dihydro-2H-indeno[5,4-b]furan-8-yl)
ethyl]propionamide, and
N-[2-(7-phenyl-1,6-dihydro-2H-indeno[5,4-b]furan-8-yl)
ethyl]butylamide.
Particularly preferred examples thereof include:
(S)—N-[2-(1,6,7,8-tetrahydro-2H-indeno[5,4-b]furan-8-yl)
ethyl]propionamide,
N-[2-(1,6,7,8-tetrahydro-2H-furo[3,2-e]indol-8-yl)ethyl]
propionamide,
N-[2-(1,6,7,8-tetrahydro-2H-furo[3,2-e]indol-8-yl)ethyl]bu-
tylamide,
N-[2-(7-phenyl-1,6-dihydro-2H-indeno[5,4-b]furan-8-yl)
ethyl]propionamide,
N-[2-(7-phenyl-1,6-dihydro-2H-indeno[5,4-b]furan-8-yl)
ethyl]butylamide, and
N-[2-(1,6,7,8-tetrahydro-2H-indeno[5,4-b]furan-8-yl)ethyl]
acetamide.
The compound (I) is particularly preferably a compound
represented by the formula:

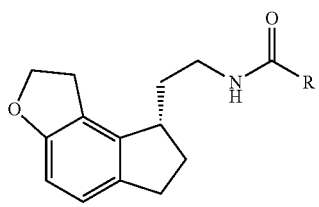

wherein R represents a $C_{1-6}$ alkyl group (for example,
methyl, ethyl, propyl, isopropyl, butyl, isobutyl, sec-butyl,
tert-butyl, pentyl, hexyl, etc.) and, for example, (S)—N-[2-
(1,6,7,8-tetrahydro-2H-indeno[5,4-b]furan-8-yl)ethyl]pro-
pionamide (hereinafter referred to as the compound A) or
(S)—N-[2-(1,6,7,8-tetrahydro-2H-indeno[5,4-b]furan-8-yl)
ethyl]acetamide (hereinafter referred to as the compound B).

As the salt of the compound (I), for example, pharma-
ceutically acceptable salts may be used. These salts include,
for example, salts with inorganic bases, salts with organic
bases, salts with inorganic acids, salts with organic acids,
salts with basic or acidic amino acids, and the like. Preferred
examples of the salts with inorganic bases include alkali
metal salts such as sodium salt, potassium salt, etc.; alkali
earth salts such as calcium salt, magnesium salt, etc.; and
aluminum salts; ammonium salts; and the like. Preferred
examples of the salts with organic bases include salts with
trimethylamine, triethylamine, pyridine, picoline, 2,6-uti-
dine, ethanolamine, diethanolamine, triethanolamine, cyclo-
hexylamine, dicyclohexylamine, N,N'-dibenzylethylenedi-
amine, etc. Preferred examples of the salts with inorganic
acids include salts with hydrochloric acid, hydrobromic
acid, nitric acid, sulfuric acid, phosphoric acid, etc. Preferred
examples of the salts with organic acids include salts with
formic acid, acetic acid, trifluoroacetic acid, phthalic acid,
fumaric acid, oxalic acid, tartaric acid, maleic acid, citric
acid, succinic acid, malic acid, methanesulfonic acid, ben-
zenesulfonic acid, p-toluenesulfonic acid, etc. Preferred
examples of the salts with basic amino acids include salts
with arginine, lysine, ornithine, etc. Preferred examples of
the salts with acidic amino acids include salts with aspartic
acid, glutamic acid, etc.

Among these salts, pharmaceutically acceptable salts are
preferred. When the compound (I) has a basic functional
group therein, examples of the salts include salts with
inorganic acids such as hydrochloric acid, hydrobromic acid,
nitric acid, sulfuric acid, phosphoric acid, etc., and salts with
organic acids such as acetic acid, phthalic acid, fumaric acid,
tartaric acid, maleic acid, citric acid, succinic acid, meth-
anesulfonic acid, p-toluenesulfonic acid, etc. When the
compound (I) has an acidic functional group therein,
examples of the salts include salts with inorganic bases
include, for example, alkali metal salts such as sodim salt,
potassium salt, etc.; alkali earth salts such as calcium salt,
magnesium salt, etc.; ammonium salts; and the like.

In addition, the compound (I) may be a hydrate or
non-hydrate.

The compound (I) can be manufactured in accordance
with a known method described in WO97/32871 (Japanese
U.S. Pat. No. 2,884,153) or a method analogous thereto.

Other preferred examples of the "unstable drug in a
polyethylene glycol-containing preparation" of the present
invention include a compound represented by the formula:

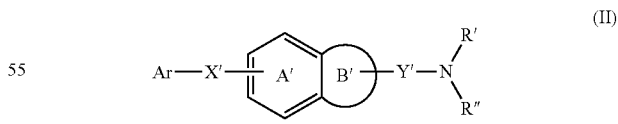

wherein Ar represents an optionally substituted aromatic
group, X' represents a divalent $C_{1-6}$ aliphatic hydrocarbon
group which may have 1 or 2 divalent groups selected from
—O—, —S—, —CO—, —SO—, —SO$_2$— and —COO—,
Y' represents a divalent $C_{1-6}$ aliphatic hydrocarbon group, R'
and R" may be the same or different and each represents a
hydrogen atom or an optionally substituted $C_{1-6}$ alkyl, ring
A' represents a benzene ring which may be further substi-
tuted, and ring B' represents a 4- or 8-membered ring which may be further substituted, or salt thereof (hereinafter referred to as the compound (II), sometimes).

Ar in the compound (II) represents an optionally substituted aromatic group.

As the "aromatic group" of the "optionally substituted aromatic group" represented by Ar, for example, there can be used a monocyclic aromatic group, a ring-assembled aromatic group, a condensed aromatic group, and the like.

As the "monocyclic aromatic group", for example, there can be used a monovalent group which can be obtained by eliminating any one hydrogen atom from a benzene ring or a 5- or 6-membered aromatic heterocyclic ring.

As the "5- or 6-membered aromatic heterocyclic ring", for example, a 5- or 6-membered aromatic heterocyclic ring containing one or more hetero atoms (for example, 1 to 3, and preferably 1 to 2 hetero atoms) selected from a nitrogen atom, a sulfur atom and an oxygen atom, in addition to carbon atoms. For example, thiophene, furan, pyrrole, imidazole, pyrazole, thiazole, oxazole, pyridine, pyrazine, pyrimidine, pyridazinering, etc., can be used.

As the monocyclic aromatic group, for example, phenyl, 2- or 3-thienyl, 2- or 3-furyl, 1-, 2- or 3-pyrrolyl, 2- or 4-imidazolyl, 3- or 4-pyrazolyl, 2-, 4- or 5-thiazolyl, 2-, 4- or 5-oxazolyl, 2-, 3- or 4-pyridyl, 2-pyrazinyl, 2-, 4- or 5-pyrimidinyl, 3- or 4-pyridazinyl, etc., can be used. Among these, preferred are phenyl, etc.

As the "ring-assembled aromatic group", for example, there can be used a group obtained by eliminating any one hydrogen atom from an aromatic ring assembly wherein 2 or more (preferably 2 or 3) aromatic rings are directly binded by a single bond and the number of bonds bonding directly the rings is smaller than the number of the ring system by one. As the "aromatic ring", aromatic hydrocarbon, aromatic heterocyclic ring, etc., are used.

As the "aromatic hydrocarbon", for example, there can be used $C_{6-14}$ monocyclic or condensed polycyclic (for example, dicyclic or tricyclic) aromatic hydrocarbon (for example, benzene, naphthalene, indene, anthracene, etc.), and the like.

As the "aromatic heterocyclic ring", for example, there can be used a 5- to 14-membered, and preferably 5- to 10-membered aromatic heterocyclic ring containing one or more (for example, 1 to 4, and preferably 1 to 2) hetero atoms selected from a nitrogen atom, a sulfur atom and an oxygen atom, in addition to carbon atoms, and the like. For example, there can be used aromatic heterocyclic ring such as thiophene, benzothiophene, benzofuran, benzimidazole, benzoxazole, benzothiazole, benzisothiazole, naphtho[2,3-b]thiophene, furan, phenoxathiin, pyrrole, imidazole, pyrazole, oxazole, isoxazole, 1,2,4-oxadiazole, 1,3,4-oxadiazole, 1,2,4-thiadiazole, 1,3,4-thiadiazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, furazan, phenoxazine, phthalimide, 2-, 3- or 4-pyridone, 2-, 3- or 4-quinolone, etc., and ring formed by condensing these rings (preferably monocyclic ring) with 1 to plural (preferably 1 or 2) aromatic rings (for example, benzenering, etc.), and the like.

As the aromatic ring assembly wherein these aromatic rings are directly bonded by a single bond, for example, there can be used an aromatic ring assembly formed of 2 or 3 (preferably 2) rings selected from a benzene ring, a naphthalene ring and a 5- to 10-membered (preferably 5- or 6-membered) aromatic heterocyclic ring, and the like. Preferred examples of the aromatic ring assembly include aromatic ring assemblies composed of 2 or 3 aromatic rings selected from benzene, naphthalene, pyridine, pyrimidine, thiophene, furan, thiazole, isothiazole, oxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran. For example, there can be used 2-, 3- or 4-biphenylyl, 3-(1-naphthyl)-1,2,4-oxadiazole-5-yl, 3-(2-naphthyl)-1,2,4-oxadiazole-5-yl, 3-(2-benzofuranyl)-1,2,4-oxadiazole-5-yl, 3-phenyl-1,2,4-oxadiazole-5-yl, 3-(2-benzoxazolyl)-1,2,4-oxadiazole-2-yl, 3-(3-indolyl)-1,2,4-oxadiazole-2-yl, 3-(2-indolyl)-1,2,4-oxadiazole-2-yl, 4-phenylthiazole-2-yl, 4-(2-benzofuranyl)thiazole-2-yl, 4-phenyl-1,3-oxazole-5-yl, 5-phenylisothiazole-4-yl, 5-phenyloxazole-2-yl, 4-(2-thienyl)phenyl, 4-(3-thienyl)phenyl, 3-(3-pyridyl)phenyl, 4-(3-pyridyl)phenyl, 6-phenyl-3-pyridyl, 5-phenyl-1,3,4-oxadiazole-2-yl, 4-(2-naphthyl)phenyl, 4-(2-benzofuranyl)phenyl, 4,4'-terphenyl, etc., and the like. Among these, biphenylyl (2-, 3- or 4-biphenylyl) is particularly preferred.

As the "condensed aromatic group", there can be used monovalent group obtained by eliminating any one hydrogen atom from a condensed polycyclic (preferably dicyclic to tetracyclic, and preferably dicyclic or tricyclic) aromatic ring, and the like. As the "condensed polycyclic aromatic ring", a condensed polycyclic aromatic hydrocarbon, a condensed polycyclic aromatic heterocyclic ring, etc. can be used.

As the "condensed polycyclic aromatic hydrocarbon", for example, a $C_{9-14}$ condensed polycyclic (dicyluc or tricyclic) aromatic hydrocarbon (for example, naphthalene, indene, anthracene, etc.), and the like, can be used.

As the "condensed polycyclic aromatic heterocyclic ring", for example, there can be used a 9- to 14-membered, and preferably 9- or 10-membered condensed polycyclic aromatic heterocyclic ring containing one or more (for example, 1 to 4) hetero atoms selected from a nitrogen atom, a sulfur atom and an oxygen atom, in addition to carbon atoms, and the like. Specifically, there can be used an aromatic heterocyclic ring such as benzofuran, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalimide, etc.

Specific examples of the above-mentioned condensed aromatic group include 1-naphthyl, 2-naphthyl, 2-quinolyl, 3-quinolyl, 4-quinolyl, 2-benzofuranyl, 2-benzothiazolyl, 2-benzimidazolyl, 1-indolyl, 2-indolyl, 3-indolyl, etc. Among these, preferred are 1-naphthyl, 2-naphthyl, and the like.

As the substituent of the aromatic group represented by Ar, for example, there can be used a halogen atom (for example, fluorine, chlorine, bromine, iodine, etc.), $C_{1-3}$ alkylenedioxy (for example, methylenedioxy, ethylenedioxy, etc.), nitro, cyano, optionally halogenated $C_{1-6}$ alkyl, $C_{6-10}$ aryloxy-$C_{1-6}$ alkyl (for example, phenoxymethyl, etc.), $C_{1-6}$ alkyl-$C_{6-10}$ aryl-$C_{2-6}$ alkenyl (for example, methylphenylethenyl, etc.), optionally halogenated $C_{3-6}$ cycloalkyl, optionally substituted $C_{7-16}$ aralkyl, optionally halogenated $C_{1-6}$ alkoxy, optionally halogenated $C_{1-6}$ alkylthio, hydroxy, optionally substituted $C_{6-10}$ aryloxy, $C_{6-10}$ aryl-$C_{7-16}$ aralkyloxy (for example, phenylbenzyloxy, etc.), amino, mono-$C_{1-6}$ alkylamino (for example, methylamino, ethylamino, propylamino, isopropylamino, butylamino, etc.), di-$C_{1-6}$ alkylamino (for example, dimethylamino, diethylamino, dipropylamino, dibutylamino, ethylmethylamino, etc.), optionally substituted 5- or 7-membered saturated cyclic amino, acyl, acylamino, acyloxy, etc. The "aromatic group"

may have 1 to 5, and preferably 1 to 3 substituents at its substitutable positions and, when the number of substituents is 2 or more, the respective substituents may be the same or different.

Among the substituent of the aromatic group represented by Ar, as the "$C_{7-16}$ aralkyl" of the "optionally substituted $C_{7-16}$ aralkyl", for example, benzyl, phenethyl, naphthylmethyl, etc., can be used.

As the "$C_{6-10}$ aryloxy" of the "optionally substituted $C_{6-10}$ aryloxy", for example, phenyloxy, naphthyloxy, etc., can be used. As the "substituent" of the "optionally substituted $C_{7-16}$ aralkyl" and the "optionally substituted $C_{6-10}$ aryloxy", for example, there can be used 1 to 5 substituents such as a halogen atom (for example, fluorine, chlorine, bromine, iodine, etc.), $C_{1-3}$ alkylenedioxy (for example, methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (for example, methylamino, ethylamino, propylamino, isopropylamino, butylamino, etc.), di-$C_{1-6}$ alkylamino (for example, dimethylamino, diethylamino, dipropylamino, dibutylamino, ethylmethylamino, etc.), formyl, carboxy, carbamoyl, optionally halogenated $C_{1-6}$ alkyl-carbonyl, $C_{1-6}$ alkoxy-carbonyl (for example, methoxycarbonyl, ethoxycarbonyl, propoxycarbonyl, tert-butoxycarbonyl, etc.), mono-$C_{1-6}$ alkyl-carbamoyl (for example, methylcarbamoyl, ethylcarbamoyl, etc.), di-$C_{1-6}$ alkyl-carbamoyl (for example, dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamide, $C_{1-6}$ alkoxy-carboxamide (for example, methoxycarboxamide, ethoxycarboxamide, propoxycarboxamide, butoxycarboxamide, etc.), $C_{1-6}$ alkylsulfonylamino (for example, methylsulfonylamino, ethylsulfonylamino, etc.), $C_{1-6}$ alkyl-carbonyloxy (for example, acetoxy, propanoyloxyoxy, etc.), $C_{1-6}$ alkoxy-carbonyloxy (for example, methoxycarbonyloxy, ethoxycarbonyloxy, propoxycarbonyloxy, butoxycarbonyloxy, etc.), mono-$C_{1-6}$ alkyl-carbamoyloxy (for example, methylcarbamoyloxy, ethylcarbamoyloxy, etc.) and di-$C_{1-6}$ alkyl-carbamoyloxy (for example, dimethylcarbamoyloxy, diethylcarbamoyloxy, etc.), and the like, respectively.

Among the substituent of the aromatic group represented by Ar, as the "5- or 7-membered saturated cyclic amino" of the "optionally substituted 5- or 7-membered saturated cyclic amino", for example, morpholino, thiomorpholino, piperazin-1-yl, piperidino, pyrrolidin-1-yl, hexamethylen-1-yl, etc., can be used. As the "substituent" of the "optionally substituted 5- or 7-membered saturated cyclic amino", for example, there can be used 1 to 3 substituents such as optionally halogenated $C_{1-6}$ alkyl, optionally substituted $C_{6-14}$ aryl, optionally substituted $C_{7-19}$ aralkyl, optionally substituted 5- to 10-membered aromatic heterocyclic group, optionally substituted $C_{6-10}$ aryl-carbonyl, optionally halogenated $C_{1-6}$ alkyl-carbonyl, optionally halogenated $C_{1-6}$ alkylsulfonyl, etc.

As the "$C_{6-14}$ aryl" of the "optionally substituted $C_{6-14}$ aryl", for example, phenyl, 1-naphthyl, 2-naphthyl, 2-indenyl, 2-anthryl, etc., can be used. Among these, phenyl is preferred. As the "$C_{7-19}$ aralkyl" of the "optionally substituted $C_{7-19}$ aralkyl", for example, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc., can be used. Among these, benzyl is preferred. As the "5- to 10-membered aromatic heterocyclic group" of the "optionally substituted 5- to 10-membered aromatic heterocyclic group", for example, 2-, 3- or 4-pyridyl, 1-, 2- or 3-indolyl, 2- or 3-thienyl, etc., can be used. Among these, 2-, 3- or 4-pyridyl is preferred. The "$C_{6-10}$ aryl-carbonyl" of the "optionally substituted $C_{6-10}$ aryl-carbonyl" includes, for example, benzoyl, 1-naphthoyl, 2-naphthoyl, etc. As the substituent with which the "optionally substituted $C_{6-14}$ aryl", the "optionally substituted $C_{7-19}$ aralkyl", the "optionally substituted 5- to 10-membered aromatic heterocyclic group" and the "optionally substituted $C_{6-10}$ aryl-carbonyl" may be substituted, there can be used 1 to 5 substituents such as a halogen atom (for example, fluorine, chlorine, bromine, iodine, etc.), $C_{1-3}$ alkylenedioxy (for example, methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (for example, methylamino, ethylamino, propylamino, isopropylamino, butylamino, etc.), di-$C_{1-6}$ alkylamino (for example, dimethylamino, diethylamino, dipropylamino, dibutylamino, ethylmethylamino, etc.), formyl, carboxy, carbamoyl, optionally halogenated $C_{1-6}$ alkyl-carbonyl, $C_{1-6}$ alkoxy-carbonyl (for example, methoxycarbonyl, ethoxycarbonyl, propoxycarbonyl, tert-butoxycarbonyl, etc.), mono-$C_{1-6}$ alkyl-carbamoyl (for example, methylcarbamoyl, ethylcarbamoyl, etc.), di-$C_{1-6}$ alkyl-carbamoyl (for example, dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamide, $C_{1-6}$ alkoxy-carboxamide (for example, methoxycarboxamide, ethoxycarboxamide, propoxycarboxamide, butoxycarboxamide, etc.), $C_{1-6}$ alkylsulfonylamino (for example, methylsulfonylamino, ethylsulfonylamino, etc.), $C_{1-6}$ alkyl-carbonyloxy (for example, acetoxy, propanoyloxyoxy, etc.), $C_{1-6}$ alkoxy-carbonyloxy (for example, methoxycarbonyloxy, ethoxycarbonyloxy, propoxycarbonyloxy, butoxycarbonyloxy, etc.), mono-$C_{1-6}$ alkyl-carbamoyloxy (for example, methylcarbamoyloxy, ethylcarbamoyloxy, etc.), di-$C_{1-6}$ alkyl-carbamoyloxy (for example, dimethylcarbamoyloxy, diethylcarbamoyloxy, etc.), etc.

As the "acyl" as the "substituent" of the "optionally substituted aromatic group" represented by Ar as well as "acyl" of "acylamino" and "acyloxy", for example, there can be used acyl represented by the formula: —CO—$R^a$, —CO—$OR^a$, —CO—$NR^aR^a$, —CS—$NHR^a$, —$SO_2$—$R^{aa}$ or —SO—$R^{aa}$ wherein $R^a$ represents (i) a hydrogen atom, (ii) an optionally substituted hydrocarbon group, for example, a hydrocarbon group which may have 1 to 5 substituents selected from a halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, optionally substituted 5- or 7-membered cyclic amino, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamide, $C_{6-10}$ aryl-carboxamide, $C_{1-6}$ alkoxy-carboxamide, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or (iii) an optionally substituted heterocyclic group, for example, a heterocyclic group which may have 1 to 5 substituents selected from a halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, optionally substituted 5- or 7-membered cyclic amino, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamide, $C_{6-10}$ aryl-carboxamide, $C_{1-6}$ alkoxy-carboxamide, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, $R^{aa}$ represents (i) an optionally substituted hydrocarbon group, for example, a hydrocarbon group which may have 1 to 5 substituents selected from a halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, optionally substituted 5- or 7-membered cyclic amino, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamide, $C_{6-10}$ aryl-carboxamide, $C_{1-6}$ alkoxy-carboxamide, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or (ii) an optionally substituted heterocyclic group which may have 1 to 5 substituents, for example, a heterocyclic group which may have 1 to 5 substituents selected from a halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, optionally substituted 5- or 7-membered cyclic amino, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamide, $C_{6-10}$ aryl-carboxamide, $C_{1-6}$ alkoxy-carboxamide, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, and $R^b$ represents a hydrogen atom or $C_{1-6}$ alkyl, or $R^a$ and $R^b$ may be combined with the adjacent nitrogen atoms to form a nitrogen-containing heterocyclic ring.

As the "optionally substituted 5- or 7-membered saturated cyclic amino" as the substituent of $R^a$ and $R^{aa}$, there can be used the same one as that described above.

As the hydrocarbon group represented by $R^a$ and $R^{aa}$, there can be used a group obtained by eliminating one hydrogen atom from the hydrocarbon compound and, for example, a chainlike or cyclic hydrocarbon group (for example, alkyl, alkenyl, alkynyl, cycloalkyl, aryl, aralkyl, etc.), etc., can be used. Among these, preferred is the following $C_{1-19}$ chainlike or cyclic hydrocarbon group:

(a) $C_{1-6}$ alkyl (for example, methyl, ethyl, propyl, isopropyl, butyl, isobutyl, sec-butyl, tert-butyl, pentyl, hexyl, etc.), (b) $C_{2-6}$ alkenyl (for example, vinyl, allyl, isopropenyl, 2-butenyl, etc.), (c) $C_{2-6}$ alkynyl (for example, ethynyl, propargyl, 2-butynyl, etc.), (d) $C_{3-6}$ cycloalkyl (for example, cyclopropyl, cyclobutyl, cyclopentyl, cyclohexyl, etc.), $C_{3-6}$ cycloalkyl may being condensed with one benzene ring, (e) $C_{6-14}$ aryl (for example, phenyl, 1-naphthyl, 2-naphthyl, 2-indenyl, 2-anthryl, etc.), preferably phenyl, and (f) $C_{7-19}$ aralkyl (for example, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.), preferably benzyl.

As the heterocyclic group represented by $R^a$ and $R^{aa}$, for example, there can be used a 5- to 14-membered (monocylic, dicyclic or tricyclic) heterocyclic ring containing one or two kinds of 1 to 4 (preferably, 1 to 3) hetero atoms selected from a nitrogen atom, a sulfur atom and an oxygen atom, in addition to carbon atoms, preferably, (i) a 5- to 14-membered (preferably 5- to 10-membered) aromatic heterocyclic ring, (ii) a 5- to 10-membered non-aromatic heterocyclic ring or (iii) a monovalent group obtained by eliminating any one hydrogen atom from 7- to 10-membered bridged heterocyclic ring, and the like.

As the "5- to 14-membered (preferably, 5- to 10-membered) aromatic heterocyclic ring", for example, there can be used an aromatic heterocyclic ring such as thiophene, benzothiophene, benzofuran, benzimidazole, benzoxazole, benzothiazole, benzisothiazole, naphtho[2,3-b]thiophene, furan, phenoxathiin, pyrrole, imidazole, pyrazole, oxazole, 1,2,4-oxadiazole, 1,3,4-oxadiazole, 1,2,4-thiadiazole, 1,3,4-thiadiazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc., or rings formed by condensing these rings (preferably, monocyclic ring) with 1 to plural (preferably, 1 or 2) aromatic rings (for example, benzenering, etc.), and the like.

As the "5- to 10-membered non-aromatic heterocyclic ring", for example, pyrrolidine, imidazoline, pyrazolidine, pyrazoline, piperidine, piperazine, morpholine, thiomorpholine, etc., can be used. As the "7- to 10-membered bridged heterocyclic ring", for example, quinuclidine, 7-azabicyclo [2.2.1]heptane, etc., can be used.

The "heterocyclic group" is preferably a 5- to 10-membered (monocyclic or dicyclic) heterocyclic group containing one or two kinds of 1 to 4 hetero atoms selected from a nitrogen atom, a sulfur atom and an oxygen atom, in addition to carbon atoms. Specific examples thereof include an aromatic heterocyclic group such as 2- or 3-thienyl, 2-,3- or 4-pyridyl, 2- or 3-furyl, 2-, 3-, 4-, 5- or 8-quinolyl, 4-isoquinolyl, pyrazinyl, 2- or 4-pyrimidinyl, 3-pyrrolyl, 2-imidazolyl, 3-pyridazinyl, 3-isothiazolyl, 3-isooxazolyl, 1-indolyl, 2-indolyl, 2-isoindolinyl, etc., and a non-aromatic heterocyclic group such as 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc. Among these, 5- to 6-membered heterocyclic group containing 1 to 3 hetero atoms selected from nitrogen atom, sulfur atom and oxygen atom, in addition to carbon atoms, is preferred and, for example, there can be used 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isooxazolyl, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc.

As the "$C_{1-6}$ alkyl" represented by $R^b$, for example, methyl, ethyl, propyl, isopropyl, butyl, isobutyl, sec-butyl, tert-butyl, pentyl, hexyl, etc., can be used.

As the "nitrogen-containing heterocyclic ring" formed by combining $R^a$ and $R^b$ with the adjacent nitrogen atom, for example, there can be used a 5- or 7-membered nitrogen-containing heterocyclic ring which contains at least one nitrogen atom and also contains 1 to 3 hetero atoms selected from a nitrogen atom, a sulfur atom and an oxygen atom, in addition to carbon atoms, and examples theerof include piperidine, morpholine, thiomorpholine, piperazine, pyrrolidine, etc.

Preferred examples of the "acyl" as the "substituent" of the "aromatic group" represented by Ar include formyl, carboxy, carbamoyl, optionally halogenated $C_{1-6}$ alkyl-carbonyl, $C_{1-6}$ alkoxy-carbonyl (for example, methoxycarbonyl, ethoxycarbonyl, propoxycarbonyl, tert-butoxycarbonyl, etc.), optionally substituted $C_{6-10}$ aryl-carbonyl, optionally substituted $C_{6-10}$ aryloxy-carbonyl, optionally substituted $C_{7-16}$ aralkyloxy-carbonyl, optionally substituted 5- to 6-membered heterocyclic carbonyl, mono-$C_{1-6}$ alkyl-carbamoyl, di-$C_{1-6}$ alkyl-carbamoyl (for example, dimethylcarbamoyl, diethylcarbamoyl, ethylmethylcarbamoyl, etc.), optionally substituted $C_{6-10}$ aryl-carbamoyl, optionally substituted 5- to 6-membered heterocyclic carbamoyl, optionally halogenated $C_{1-6}$ alkylsulfonyl, optionally substituted $C_{6-10}$ arylsulfonyl, etc.

Among these, as the "$C_{6-10}$ aryl-carbonyl" of the "optionally substituted $C_{6-10}$ aryl-carbonyl", for example, benzoyl, 1-naphthoyl, 2-naphthoyl, etc., can be used. As the "$C_{6-10}$ aryloxy-carbonyl" of the "optionally substituted $C_{6-10}$ aryloxy-carbonyl", for example, phenoxycarbonyl, etc., can be used. As the "$C_{7-16}$ aralkyloxy-carbonyl" of the "optionally substituted $C_{7-16}$ aralkyloxy-carbonyl", for example, benzyloxycarbonyl, phenethyloxycarbonyl, etc. can be used. As the "5- to 6-membered heterocyclic carbonyl" of the "optionally substituted 5- to 6-membered heterocyclic carbonyl", for example, nicotinoyl, isonicotinoyl, 2-thenoyl, 3-thenoyl, 2-furoyl, 3-furoyl, morpholinocarbonyl, piperidinocarbonyl, 1-pyrrolidinylcarbonyl, etc., can be used. As the "$C_{6-10}$ aryl-carbamoyl" of the "optionally substituted $C_{6-10}$ aryl-carbamoyl", for example, phenylcarbamoyl, 1-naphthylcarbamoyl, 2-naphthylcarbamoyl, etc., can be used. As the "5- to 6-membered heterocyclic carbamoyl" of the "optionally substituted 5- to 6-membered heterocyclic carbamoyl", for example, 2-pyridylcarbamoyl, 3-pyridylcarbamoyl, 4-pyridylcarbamoyl, 2-thienylcarbamoyl, 3-thienylcarbamoyl, etc., can be used. As the "$C_{6-10}$ arylsulfonyl" of the "optionally substituted $C_{6-10}$ arylsulfonyl", for example, benzenesulfonyl, 1-naphthalenesulfonyl, 2-naphthalenesulfonyl, etc., can be used.

As the "substituent" of these "optionally substituted $C_{6-10}$ aryl-carbonyl", "optionally substituted $C_{6-10}$ aryloxy-carbonyl", "optionally substituted $C_{7-16}$ aralkyloxy-carbonyl", "optionally substituted 5- to 6-membered heterocyclic carbonyl", "optionally substituted $C_{6-10}$ aryl-carbamoyl", "optionally substituted 5- to 6-membered heterocyclic carbamoyl" and "optionally substituted $C_{6-10}$ arylsulfonyl", for example, there can be used 1 to 5, and preferably 1 to 3 substituents selected from a halogen atom, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl, carboxy, carbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy.

As the "acylamino" which is the "substituent" of the "optionally substituted aromatic group" represented by Ar, for example, there can be used amino substituted with 1 to "acyl" groups described in detail as for the "substituent" of the "optionally substituted aromatic group" represented by Ar, preferably, acylamino represented by the formula: —$NR^c$—$COR^d$, —$NR^c$—$COOR^{da}$, —$NR^c$—$SO_2RR^{da}$ or —$NR^c$—$CONR^{da}R^{db}$ wherein $R^c$ represents a hydrogen atom or $C_{1-6}$ alkyl, $R^d$ is as defined with respect to $R^a$, $R^{da}$ is as defined with respect to $R^{aa}$, and $R^{db}$ is as defined with respect to $R^b$, and the like.

The "$C_{1-6}$ alkyl" represented by $R^c$ and $R^{db}$ used may be the same "$C_{1-6}$ alkyl" as that represented by $R^b$.

As the "acylamino" which is the "substituent" of the "optionally substituted aromatic group" represented by Ar, for example, there can be used formylamino, optionally halogenated $C_{1-6}$ alkyl-carboxamide, optionally substituted $C_{6-10}$ aryl-carboxamide (for example, phenylcarboxamide, naphthylcarboxamide, etc.), $C_{1-6}$ alkoxy-carboxamide (for example, methoxycarboxamide, ethoxycarboxamide, propoxycarboxamide, butoxycarboxamide, etc.), $C_{1-6}$ alkylsulfonylamino (for example, methylsulfonylamino, ethylsulfonylamino, etc.), and the like.

As the "acyloxy" which is the "substituent" of the "optionally substituted aromatic group" represented by Ar, for example, there can be used oxy substituted with one "acyl" described in detail as for the "substituent" of the "optionally substituted aromatic group", and preferably acyloxy represented by the formula: —O—$COR^e$, —O—CO-$OR^e$ or —O—$CONHR^e$ wherein $R^e$ has the same meansing as in $R^a$, and the like.

As the "acyloxy" which is the "substituent" of the "optionally substituted aromatic group" represented by Ar, there can be preferably used $C_{1-6}$ alkyl-carbonyloxy (for example, acetoxy, propanoyloxyoxy, etc.), optionally substituted $C_{6-10}$ aryl-carbonyloxy (for example, benzoyloxy, 1-naphthoyloxy, 2-naphthoyloxy, etc.), $C_{1-6}$ alkoxy-carbonyloxy (for example, methoxycarbonyloxy, ethoxycarbonyloxy, propoxycarbonyloxy, butoxycarbonyloxy, etc.), mono-$C_{1-6}$ alkyl-carbamoyloxy (for example, methylcarbamoyloxy, ethylcarbamoyloxy, etc.), di-$C_{1-6}$ alkyl-carbamoyloxy (for example, dimethylcarbamoyloxy, diethylcarbamoyloxy, etc.), optionally substituted $C_{6-10}$ aryl-carbamoyloxy (for example, phenylcarbamoyloxy, naphthylcarbamoyloxy, etc.), nicotinoyloxy, and the like. As the "substituent" of these "optionally substituted $C_{6-10}$ aryl-carboxamide", "optionally substituted $C_{6-10}$ aryl-carbonyloxy" and "optionally substituted $C_{6-10}$ aryl-carbamoyloxy" and "preferred examples" thereof, there can be used the same "substituent" as that in "optionally substituted $C_{6-10}$ aryl-carbonyl".

Among these, Ar is preferably an optionally substituted ring-assembled aromatic group (particularly, biphenylyl such as 2-, 3- or 4-biphenylyl, etc.).

X' in the compound (II) represents a divalent $C_{1-6}$ aliphatic hydrocarbon group which may have 1 or 2 divalent groups selected from —O—, —S—, —CO—, —SO—, —SO$_2$— and —COO—, and Y' represents a divalent $C_{1-6}$ aliphatic hydrocarbon group.

As the $C_{1-6}$ aliphatic hydrocarbon group, $C_{1-6}$ alkylene, $C_{2-6}$ alkenylene, $C_{2-6}$ alkynylene, etc., can be used.

As the $C_{1-6}$ alkylene, for example, there can be used straight chainlike $C_{1-6}$ alkylene such as —CH$_2$—, —(CH$_2$)$_2$—, —(CH$_2$)$_3$—, —(CH$_2$)$_4$—, —(CH$_2$)$_5$—, —(CH$_2$)$_6$—, etc., $C_{1-3}$ alkylene (for example, —CH$_2$—, —(CH$_2$)$_2$—, —(CH$_2$)$_3$—, etc.) which may have 1 to 3 $C_{1-3}$ alkyl groups, and the like.

As the $C_{2-6}$ alkenylene, for example, there can be used straight chainlike $C_{2-6}$ alkenylene such as —CH=CH—, —CH$_2$—CH=CH—, etc., $C_{2-3}$ alkenylene (for example, —CH=CH—, —CH$_2$—CH=CH—, etc.) which may have 1 to 3 $C_{1-3}$ alkyl groups, and the like.

As the $C_{2-6}$ alkynylene, for example, there can be used straight-chain $C_{2-6}$ alkynylene such as —C≡C—, —CH$_2$—C≡C—, —C≡C—CH$_2$—, —C≡C—CH$_2$CH$_2$—, —CH$_2$CH$_2$—C≡C—, —CH$_2$—C≡C—CH$_2$—, —(CH$_2$)$_2$—C≡C—CH$_2$—, —(CH$_2$)$_2$—C≡C—(CH$_2$)$_2$—, —(CH$_2$)$_3$—C≡C—CH$_2$—, etc., $C_{2-3}$ alkynylene (for example, —C≡C—, —CH$_2$—C≡C—, —C≡C—CH$_2$—, —C≡C—CH$_2$CH$_2$—, —CH$_2$CH$_2$—C≡C—, etc.) which may have 1 to 3 $C_{1-3}$ alkyl groups.

As the $C_{1-6}$ aliphatic hydrocarbon group, particularly preferred is a $C_{1-3}$ aliphatic hydrocarbon group such as $C_{1-3}$ alkylene, $C_{2-3}$ alkenylene, $C_{2-6}$ alkynylene, etc.

Particularly, X' is preferably $C_{1-3}$ alkylene having one —O— and Y' is preferably $C_{1-3}$ alkylene.

R' and R" in the compound (II) are the same or different and represent optionally substituted $C_{1-6}$ alkyl.

As the "$C_{1-6}$ alkyl" of the "optionally substituted $C_{1-6}$ alkyl" in R' and R", for example, methyl, ethyl, propyl, isopropyl, butyl, isobutyl, sec-butyl, tert-butyl, pentyl, hexyl, etc., can be used. Among these, methyl, ethyl and propyl, etc., are preferred.

As the "substituent" of the "optionally substituted $C_{1-6}$ alkyl" represented by R' or R", for example, there can be used 1 to 5, and preferably 1 to 3 substituents such as a halogen atom (for example, fluorine, chlorine, bromine, iodine, etc.), $C_{1-3}$ alkylenedioxy (for example, methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (for example, methylamino, ethylamino, propylamino, isopropylamino, butylamino, etc.), di-$C_{1-6}$ alkylamino (for example, dimethylamino, diethylamino, dipropylamino, dibutylamino, ethylmethylamino, etc.), formyl, carboxy, carbamoyl, optionally halogenated $C_{1-6}$ alkyl-carbonyl, $C_{1-6}$ alkoxy-carbonyl (for example, methoxycarbonyl, ethoxycarbonyl, propoxycarbonyl, tert-butoxycarbonyl, etc.), mono-$C_{1-6}$ alkyl-carbamoyl (for example, methylcarbamoyl, ethylcarbamoyl, etc.), di-$C_{1-6}$ alkyl-carbamoyl (for example, dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamide, $C_{1-6}$ alkoxy-carboxamide (for example, methoxycarboxamide, ethoxycarboxamide, propoxycarboxamide, butoxycarboxamide, etc.), $C_{1-6}$ alkylsulfonylamino (for example, methylsulfonylamino, ethylsulfonylamino, etc.), $C_{1-6}$ alkyl-carbonyloxy (for example, acetoxy, propanoyloxyoxy, etc.), $C_{1-6}$ alkoxy-carbonyloxy (for example, methoxycarbonyloxy, ethoxycarbonyloxy, propoxycarbonyloxy, butoxycarbonyloxy, etc.), mono-$C_{1-6}$ alkyl-carbamoyloxy (for example, methylcarbamoyloxy, ethylcarbamoyloxy, etc.), di-$C_{1-6}$ alkyl-carbamoyloxy (for example, dimethylcarbamoyloxy, diethylcarbamoyloxy, etc.), optionally substituted aromatic group, and the like. When the number of substituents is 2 or more, the respective substituents may be the same or different.

The ring A' in the compound (II) represents a benzene ring which may be further substituted. That is, the ring A' may further have substituent(s) at its substitutable positions, in addition to the group represented by the formula: Ar—X'—. As the substituent, for example, there can be used a halogen atom (for example, fluorine, chlorine, bromine, iodine, etc.), optionally halogenated $C_{1-6}$ alkyl, optionally halogenated $C_{1-6}$ alkoxy, hydroxy, amino, and the like. As the "optionally halogenated $C_{1-6}$ alkyl" and "optionally halogenated $C_{1-6}$ alkoxy", there can be used the same "optionally halogenated $C_{1-6}$ alkyl" and "optionally halogenated $C_{1-6}$ alkoxy" as those described as for Ar. As the substituent of the ring A, particularly preferred are a halogen atom (for example, chlorine, etc.), $C_{1-6}$ alkoxy (for example, methoxy, etc.), etc. The ring A' may be substituted with 1 to 3 substituents at its substitutable positions and, when the number of substituents is 2 or more, the respective substituents may be the same or different. It is particularly preferred that the ring A' is substituted only with the group represented by the formula: Ar—X'—.

The ring B' in the compound (II) represents a 4- or 8-membered ring which may be further substituted.

The 4- or 8-membered ring represented by the ring B' includes, for example, 4- to 8-membered homocyclic or heterocyclic ring which may have one double bond at the portion other than that condensed with the ring A' and may contain 1 to 3 hetero atoms selected from an oxygen atom, a nitrogen atom and a sulfur atom, in addition to carbon atoms. Specific examples thereof include ring represented by the formula:

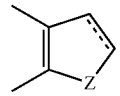

wherein ---- represents a single bond or a double bond, and Z' represents (i) bond, (ii) $C_{1-4}$ alkylene or (iii) $C_{2-4}$ alkenylene. Z' is preferably $C_{1-3}$ alkylene, and more preferably ethylene.

The "4- or 8-membered ring" is preferably a ring represented by the formula:

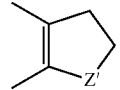

wherein Z' is as defined above, and preferably 6-membered homocyclic or heterocyclic ring which has no double bond other than that at the portion condensed with the ring A' and may contain one oxygen atom or imino, in addition to carbon atoms.

The "substituent" of the "4- or 8-membered ring which may be further substituted" represented by the ring B' includes, for example, oxo, C1-6 alkyl (for example, methyl, ethyl, propyl, isopropyl, butyl, etc.), hydroxy, and the like. The ring B' may be substituted with 1 to 3 substituents at its substitutable positions and, when the number of substituents is 2 or more, the respective substituents may be the same or different.

The ring B' is preferably a 6-membered homocyclic or heterocyclic ring which has no substituent other than the group represented by the formula:

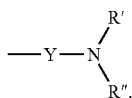

The condensed ring formed by the ring A' and the ring B' is preferably a ring represented by the formula:

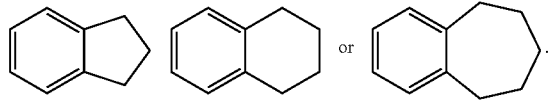

Particularly, tetralin is preferred.

The compound (I) is preferably 6-(4-biphenylyl)methoxy-2-[2-(N,N-dimethylamino)ethyl]tetralin, 6-(4-biphenylyl)methoxy-2-(N,N-dipropylamino)methyltetralin, and salts and optically active substances thereof, and particularly preferably (R)-(+)-6-(4-biphenylyl)methoxy-2-[2-(N,N-dimethylamino)ethyl]tetralin (also referred to as (R)-6-[(1,1'-biphenyl)-4-ylmethoxy]-1,2,3,4-tetrahydro-N,N-dimethyl-2-naphthaleneethanamin) hydrochloride monohydrate (compound C).

As the salt of the compound (II), for example, there can be used salts with inorganic bases, ammonium salts, salts with organic bases, salts with inorganic acids, salts with organic acids, salts with basic or acidic amino acids, and the like.

Preferred examples of the salts with inorganic bases include alkali metal salts such as sodium salt, potassium salt, etc.; alkali earth salts such as calcium salt, magnesium salt, barium salt, etc.; aluminum salts; etc. Preferred examples of the salts with organic bases include salts with trimethylamine, triethylamine, pyridine, picoline, ethanolamine, diethanolamine, triethanolamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc.

Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, toluenesulfonic acid, etc. Preferred examples of the salts with basic amino acids include salts with arginine, lysine, ornithine, etc. Preferred examples of the salts with acidic amino acids include salts with aspartic acid, glutamic acid, etc.

Among these salts, pharmaceutically acceptable salts are preferred. When the compound (II) has an acidic functional group therein, there can be used inorganic salts such as alkali metal salts (for example, sodium salt, potassium salt, etc.), alkali earth salts (for example, calcium salt, magnesium salt, barium salt, etc.) and ammonium salts. When the compound (II) has a basic functional group therein, there can be used inorganic salts such as hydrochloride, sulfate, phosphate, hydrobromide, etc.; and organic salts such as acetate, maleate, fumarate, succinate, methanesulfonate, p-toluenesulfonate, citrate, tartrate, etc.

Also the compound (II) may be a hydrate or non-hydrate. In case of the hydrate, it may have 1 to $3H_2O$ molecules.

The compound (II) may be the same prodrug as described as for the above-mentioned compound (I).

The compound (II) may be labeled by an isotope (for example, $^2H$, $^3H$, $^{14}C$, $^{35}S$, $^{125}I$, etc.).

The compound (II) can be manufactured in accordance with a known method described in JP 11-80098 A. Alternatively, as its improved method, when an amide bond and an ether bond exist in the same molecule, the compound (II) can be manufactured by selectively cleaving only the ether bond in the presence of methanesulfonic acid and methionine, and then subjecting to an alkylation reaction, followed by reducing the amide moiety.

The above-mentioned "preparation ingredients" include, for example, excipients [for example, lactose, sucrose, D-mannitol, D-sorbitol, starch (corn starch, potato starch, etc.), α-starch, dextrin, crystalline cellulose, low hydroxypropylated hydroxypropylcellulose, carboxymethylcellulose sodium, acacia, dextran, pullulan, light anhydrous silicic acid, synthetic aluminum silicate, magnesium aluminometasilicate, etc.], binders (e.g. α-starch, sucrose, gelatin, powdered acacia, methylcellulose, carboxymethylcellulose, carboxymethylcellulose sodium, hydroxypropylcellulose, hydroxypropylmethylcellulose, polyvinylpyrrolidone, crystalline cellulose, dextrin, pullulan, etc.), lubricants (for example, magnesium stearate, calcium stearate, talc, colloidal silica, etc.), disintegrators [for example, lactose, sucrose, carboxymethylcellulose, low hydroxypropylated hydroxypropylcellulose, starch (corn starch, potato starch, etc.), light anhydrous silicic acid, croscarmellose sodium, sodium carboxymethyl starch, carboxymethylcellulose calcium, etc.], colorants, flavors, corrigents, adsorbents, preservatives, moisturizers, antistatic agents, disintegration retarders, etc.

The amount of the above-mentioned preparation ingredients to be added can be one that is generally used for manufacturing a preparation.

The dosage form of the "preparation" of the present invention includes, for example, tablets, powders, granules, fine granules, pills, etc. The granules contain, for example, about 90% by weight or more of particles having a particle size of about 500 to about 1410 μm and about 5% by weight or less of particles having a particle size of about 177 μm or less. Further, the fine granules contain, for example, about 75% by weight or more of particles having a particle size of about 10 to about 500 μm, about 5% by weight or less of particles having a particle size of about 500 μm or more, and about 10% by weight or less of particles having a particle size of about 10 μm or less. The fine granules contain preferably about 75% by weight or more of particles having a particle size of about 150 to about 500 μm, about 5% by weight or less of particles having a particle size of about 500 μm or more and about 10% by weight or less of particles having a particle size of about 74 μm or less.

The "preparation" of the present invention can be manufactured by coating a "drug-containing composition" obtained by mixing the above-mentioned "drug" and "preparation ingredients" in accordance with a conventional method, with the "coating agent".

The amount of the coating agent used can be selected depending on the dosage form of the preparation. The amount of the coating agent used (dry weight) in the preparation is, for example, about 0.1 to about 30% by weight, preferably about 0.5 to about 10% by weight in case of tablets; about 0.1 to about 50% by weight, preferably about 1 to about 20% by weight in case of granules or pills; about 0.1 to about 100% by weight, preferably about 1 to about 50% by weight in case of fine granules.

As coating methods, per se known methods such as pan coating, fluidized-bed coating, agitating fluidized-bed coating, or a combination of these procedures can be employed. When the coating agent is a solution or a dispersion containing water or an organic solvent, spray-coating can also be employed.

The temperature during coating is usually about 25 to about 60° C., preferably about 25 to about 40° C.

And the time used for coating can be appropriately selected by taking into account particular coating method, characteristics or amount of the coating agent or characteristics of the pharmaceutical preparation, etc.

The above-mentioned compound (I) has an excellent melatonin action and less toxicity. Further, it is safe and causes no side effects. Thus the compound can be suited for use in the preparation of the present invention.

The "preparation" of the present invention can be used, for example, when the compound (I) or a salt thereof is used as a drug, for the prevention or treatment of diseases such as biological rhythm disorder influenced by melatonin, for example, sleep-awakening rhythm disorder, jet lag, abnormal physical conditions caused by a three-shift system, seasonal melancholia, reproduction and neuroendocrine diseases, enile dementia, Alzheimer's disease, various disorders caused by aging (for example, prevention from getting older, etc.), cerebral circulation disorder (for example, cerebral apoplexy, etc.), head injury, bone marrow injury, stress, epilepsy, paralysis, anxiety, depression, Parkinson's disease, hypertension, glaucoma, cancer, sleeplessness, diabetes, and the like. Also, it is effective to immunoregulation, modification of intelligence, ataractic or modification of ovulation (for example, contraception, etc.). Accordingly, when the compound (I) or a salt thereof is used in the pharmaceutical preparation of the present invention, the preparation can be used, for example, as a biological rhythm modifier, preferably remedy for dysgryphia (for example, a sleeping drug, etc.), a sleep-awakening rhythm modifier (also including sleep-awakening rhythm modifying action), an agent for preventing or treating time-zone syndrome and so-called jet lag, and the like.

The dosage range of the "pharmaceutical preparation" of the present invention can be selected so that an effective amount of a drug can be administered by taking into account the kind of drug, the kind of disease, conditions, a dosage form, etc. For example, when the compound (I) or a salt thereof is used as a drug, the "pharmaceutical preparation" can be administered in such an amount that a daily dosage range of the compound (I) or a salt thereof for an adult (body weight: 60 kg) is about 0.01 mg to about 100 mg, preferably about 0.1 to about 30 mg, more preferably about 0.3 to about 10 mg, and this can be administered once per day, or by dividing into 2 or 3 times per day. In particular, in case of the above-mentioned compound A or B, it can be administered in a daily dosage range of about 0.3 mg to about 64 mg.

The above-mentioned compound (II) is effective for the prevention or treatment of neurodegenerative diseases, amyloid angiopathy, nerve disorders caused by cerebrovascular disorders (for example, cerebral infarction, cerebral hemorrhage, etc.), head injury or spinal cord injury, and the like, because it has an excellent inhibitory activity of production and secretion of amyloid β protein and an excellent promotion activity of APP secretion, and further a β-selectase inhibitory activity.

The compound (II) has less toxicity and is also excellent in intracerebral transferability.

Therefore, the compound (II) is suited for use in the preparation of the present invention and is useful as an agent for preventing or treating neurodegenerative diseases; amyloid angiopathy; and nerve disorders caused by cerebrovascular disorders (for example, cerebral infarction, cerebral hemorrhage, etc.), head injury or spinal cord injury of mammals such as human, etc., in safety, and is also useful as a modifier of various mental disorders (for example, depression, anxiety, compulsive insanity, dysgryphia, etc.) caused by neurodegeneration and nerve disorders. Preferably, the compound (II) can be preferably used as an agent for preventing or treating neurodegenerative diseases (for example, Alzheimer's disease, Down's syndrome, senile dementia, Parkinson's disease, Creutzfeldt-Jakob disease, amyotroohic letaral sclerosis, diabetic neuropathy, Huntington's chorea, multiple sclerosis, etc.) and, more preferably, it is useful as a preparation for the prevention or treatment of neurodegenerative diseases (for example, Alzheimer's disease, Down's syndrome, etc.) caused by amyloid β protein. It is particularly useful as an agent for preventing or treating Alzheimer's disease.

The preparation of the compound (II) may be used in combination with other antidementia drugs (for example, acetylcholine esterase inhibitor, etc.).

The amount of the compound (II) in the preparation of the present invention is within a range from 0.1 to 100% by weight based on the entire preparation. The dosage varies depending on a particular subject of administration, route of administration, kind of disease, etc. and, for example, when the compound (II) is used as an agent for treating for Alzheimer's disease, the effective ingredient (in terms of the compound (II)) can be administered to an adult (body weight: 60 kg) in an amount of about 0.1 to 500 mg, preferably about 1 to 100 mg, and more preferably 5 to 100 mg as an oral agent. This can be administered by dividing into once to several times per day.

The present invention will be illustrated in more detail by following Reference Examples, Examples, Comparative Examples and Experimental Examples.

Reference Example 1: Synthesis of 2,3-dihydrobenzofuran-5-carbaldehyde 2,3-Dihydrobenzofuran (100.0 g, 832.3 mmol) and N,N-dimethylformamide (133.8 g, 1830.6 mmol) were mixed and heated, and phosphorus oxychloride (255.2 g, 1643.0 mmol) was added dropwise thereto at an inner temperature of 70 to 80° C. over 2 hours. The mixture was heated to an inner temperature of 80 to 90° C., stirred for 7.5 hours, cooled and then added dropwise to 1000 g of water, followed by stirring at room temperature for 5 hours. After extracting with toluene and washing in turn with water, saturated sodium bicarbonate water and water, the organic layer was concentrated under reduced pressure to obtain a toluene solution of the title compound (yield: 340 g, apparent yield: 100%)

Reference Example 2: Synthesis of ethyl (E)-3-(2,3-dihydrobenzofuran-5-yl)propenoate To 2,3-dihydrobenzofuran-5-carbaldehyde obtained Reference Example 1 (832.3 mmol)/toluene solution (340 g), triethyl phosphonoacetate (205.3 g, 915.7 mmol) was added dropwise under cooling. Then, t-butoxy sodium (88.0 g, 1187.3 mmol) suspended in toluene (530 g) was added dropwise to the resultant mixture and, after stirring the mixture for one hour, acetic acid (20 g) and water (500 g) were further added dropwise thereto. The reaction mixture was raised to room temperature and partitioned. The organic layer was washed in turn with saturated sodium bicarbonate water and water and concentrated under reduced pressure until the volume is reduced to 300 mL or less. Methanol (396 g) was added and the mixture was heated to dissolve it. Water (500 g) was added dropwise thereto at room temperature and the mixture was stirred to deposit crystals. The crystals were collected by filtration and dried under reduced pressure to obtain the title compound (yield: 161.3 g, 88.1%).

Reference Example 3: Synthesis of ethyl 3-(2,3-dihydrobenzofuran-5-yl)propionate Ethyl (E)-3-(2,3-dihydrobenzofuran-5-yl)propionate (50.0 g, 227.3 mmol) was dissolved in acetic acid (312.0 g). After replacing the atmosphere in the system with nitrogen, 5% Pd/C (4.96 g) (as dry) was added to the solution and the system was pressurized with hydrogen up to 196 to 294 kPa. The reaction was conducted at 50° C. under pressure of 196 to 294 kPa for one hour. The catalyst was removed by filtration, and then the reaction mixture was washed with acetic acid (208 g) to obtain an acetic acid solution of the title compound (yield: 569.3 g, apparent yield: 100%).

Reference Example 4: Synthesis of 3-(6,7-dibromo-2,3-dihydrobenzofuran-5-yl)propionic acid To the PPE/acetic acid solution (569.3 g, 227.3 mmol) obtained from the process of Reference Example 3, anhydrous sodium acetate (18.6 g) was added. Bromine (221.6 g) was added dropwise to the resultant mixture over 2 hours under cooling with stirring. Then, the reaction was conducted at room temperature for 4 hours and the reaction mixture was added dropwise to a cooled aqueous 15% sodium sulfite solution (670 ml), followed by stirring for 30 minutes. Acetonitrile (118 g) was added thereto and the mixture was reacted by heating under reflux for 2 hours. The mixture was gradually cooled and stirred for one hour to deposit crystals. The crystals were collected by filtration, washed with water and then dried to obtain the title compound (yield: 63.3 g, 73.2%).

Reference Example 5: Synthesis of 4,5-dibromo-1,2,6,7-tetrahydro-8H indeno[5,4-b]furan-8-one 3-(6,7-Dibromo-2,3-dihydrobenzofuran-5-yl)propionic acid (40.0 g, 114.3 mmol), o-dichlorobenzene (182 g) and N,N-dimethylformamide (0.1 g) were mixed and thionyl chloride (17.7 g, 148.8 mmol) was added dropwise thereto at an inner temperature of 42° C., followed by stirring for 30 to 40 minutes to obtain an acid chloride solution.

Then, anhydrous aluminum chloride (17.5 g, 131.5 mmol) was added in several portions with ice cooling, followed by stirring for 30 minutes. Separately, methanol (475 g) was prepared and the reaction mixture was added dropwise to this methanol to deposit crystals. To the mixture containing the deposited crystals, water (76 g) was added dropwise with cooling. After stirring for 30 minutes, the wet crystals were collected by filtration, washed in turn with methanol, water, saturated sodium bicarbonate water, water and methanol and then dried under reduced pressure to obtain the title compound (yield: 31.6 g, 92.2%).

Reference Example 6: Synthesis of 1,2,6,7-tetrahydro-8H-indeno[5,4-b]furan-8-one 4,5-Dibromo-1,2,6,7-tetrahydro-8H-indeno[5,4-b]furan-8-one (23.3 g, 70.3 mmol), anhydrous sodium acetate (14.4 g, 175.5 mmol) and methanol (373 g) were mixed and, after replacing the atmosphere in the system with nitrogen, 10% Pd/C (1.28 g) (as dry) was added to the mixture and the system was pressurized with hydrogen up to 490 kPa with stirring. The catalytic reduction reaction was conducted at 40° C. under pressure of 294 to 490 kPa for 2 hours. The catalyst was removed by filtration, the filtrate was concentrated under reduced pressure and water was further added thereto, followed by concentration under reduced pressure to effect replacement of the solvent. The mixture was cooled and stirred for one hour to effect aging. The deposited crystals were collected by filtration to obtain the title compound (yield: 14.4 g, 86.5%).

[Purification Process]

The wet crystals (13.2 g, 55.7 mmol), activated carbon Shirasagi A-1 (0.5 g) and methanol (320 g) were mixed, stirred under reflux for one hour and then filtered. The filtrate was concentrated under reduced pressure, refluxed for one hour and then cooled. Water (24 g) was added dropwise thereto with cooling and, after aging for one hour, the deposit was collected by filtration and then dried under reduced pressure to obtain the title compound (yield: 9.4 g, 96.0%).

Reference Example 7: Synthesis of (E)-(1,6,7,8-tetrahydro-2H-indeno[5,4-b]furan-8-ylidene)acetonitrile To a solution of toluene (184 g), 1,2,6,7-tetrahydro-8H-indeno[5,4-b]furan-8-one (8.5 g, 48.9 mmol) and diethyl cyanomethylphosphonate (10.4 g, 58.7 mmol), 28% sodium methoxide methanol solution (11.3 g) was added dropwise with ice cooling over one hour and the reaction was conducted for 4 hours. Water (85 g) was added dropwise to the reaction mixture and, after heating and partitioning, the organic layer was washed with water and then filtered under pressure to remove dusts. The organic layer was concentrated under reduced pressure and methanol was added, followed by concentration under reduced pressure to effect replacement of the solvent. The mixture was stirred with heating under reflux for one hour, followed by cooling and aging for one hour. The mixture containing the deposited crystals was filtered and the crystals were dried under reduced pressure to obtain the title compound (yield: 8.1 g, 84.4%).

Reference Example 8: Synthesis of (E)-2-(1,6,7,8-tetrahydro-2H-indeno[5,4-b]furan-8-ylidene)ethylamine hydrochloride To a mixed suspension of (E)-(1,6,7,8-tetrahydro-2H-indeno[5,4-b]furan-8-ylidene)acetonitrile (10.0 g, 50.7 mmol) in toluene (37.5 ml) and methanol (12.5 ml), spreading cobalt (7.22 g) and an aqueous 14.4% potassium hydroxide solution (1.4 g) were added, followed by stirring in a hydrogen atmosphere (0.2 MPa) at 34 to 50° C. for 6.5 hours. After the reaction mixture was filtered, the filtrate was partitioned by adding toluene (170 ml) and methanol (35 ml). 0.5 N Hydrochloric acid (101 ml) was added to the organic layer, followed by stirring at 25 to 30° C. for 30 minutes and partitioning. Activated carbon (1 g) was added to the aqueous layer and further stirring. Activated carbon was removed by filtration to obtain an aqueous solution of the title compound (246 g, Net: 12.0 g, yield: 99.6%).

Reference Example 9: Synthesis of (S)-2-(1,6,7,8-tetrahydro-2H-indeno[5,4-b]furan-6-yl)ethylamine hydrochloride To an aqueous solution of (E)-2-(1,6,7,8-tetrahydro-2H-indeno[5,4-b]furan-8-ylidene)ethylamine hydrochloride (246 g, Net: 12.0 g, 50.5 mmol), toluene (44.4 ml) and an aqueous 5% sodium hydroxide solution (40.2 g) were added, followed by stirring at 22 to 26° C. for one hour. After partitioning, methanol (7 ml) and [RuCl(benzene)(R)-BI-NAP]Cl (0.0922 g) were added to the organic layer in a nitrogen atmosphere, followed by stirring in a hydrogen atmosphere (4.9 MPa) at 70° C. for 15 hours. The reaction mixture was cooled and water (17.6 g) and 1 N hydrochloric acid (38.7 ml) were added thereto at 0 to 10° C., followed by stirring for 30 minutes and further partitioning. Pd—C (50% wet, 1.9 g) was added to the aqueous layer, followed by stirring in a hydrogen atmosphere (4.9 MPa) at 50° C. for 3 hours. After filtration, the organic layer was concentrated under reduced pressure and the residue (10.2 g) was recrystallized from a mixed solution of normal butanol and water to obtain the title compound (8.44 g, yield: 69.7%). The optical purity of this hydrochloride was measured by high performance liquid chromatography. As a result, it was 100% ee.

Reference Example 10: Synthesis of (S)—N-[2-(1,6,7,8-tetrahydro-2H-indeno[5,4-b]furan-8-yl)ethyl]acetamide (Compound B)

To a solution of (S)-2-(1,6,7,8-tetrahydro-2H-indeno[5,4-b]furan-8-yl)ethylamine hydrochloride (20.0 g, 83.4 mmol) in tetrahydrofuran (50 ml), aqueous 2 N sodium hydroxide solution (96 ml) and acetic anhydride (4.5 ml) were added, followed by stirring at room temperature for one hour. Pure water (200 ml) and seed crystal (10 mg) were added thereto and the mixture was cooled. The deposited crystals were collected by filtration and then dried under reduced pressure to obtain the title compound (9.71 g, yield: 94.8%).
[Purification Process]
The above-mentioned crystals (9.00 g, 36.7 mmol) were dissolved in ethanol (28 ml), activated carbon (90 mg) was added thereto and the mixture was stirred for 5 minutes. The mixture was filtered and water (72 ml) was added to the filtrate with warming. The mixture was cooled and the deposited crystals were collected by filtration and then dried under reduced pressure to obtain the title compound (8.64 g, yield: 96.0%).

Reference Example 11

Synthesis of (R)-(+)-6-(4-biphenylyl)methoxy-2-[2-(N,N-dimethylamino)ethyl]tetralin hydrochloride monohydrate (Compound C)

(+)-N,N-Dimethyl-(6-(4-biphenylyl)methoxy-2-tetralin)acetamide (manufactured by the method described in JP 11-310561 A) (695 g) was suspended in toluene (3475 mL) and sodium dihydro-bis(2-methoxyethoxy)aluminate (70% toluene solution) (562 g) was added dropwise thereto in a nitrogen atmosphere at an inner temperature of 20° C. or lower. After stirring at room temperature for 1.5 hours, aqueous 4N sodium hydroxide solution (695 mL) was added dropwise thereto at 20° C. or lower, followed by stirring at room temperature for 30 minutes and further partitioning. Furthermore, the organic layer was washed twice with aqueous 1N sodium hydroxide solution (695 mL) and then washed twice with water (1390 mL). Toluene (348 mL) was added to the organic layer and the mixture was heated to 60° C. and then concentrated hydrochloric acid (concentration: 36%) (175 mL) was added dropwise to the resultant mixture. After stirring with ice cooling for one hour, the deposited crystals were collected by filtration, washed with toluene (695 mL) and aqueous 50% methanol solution (1390 mL), and then dried at 40° C. under reduced pressure to obtain the title compound as pale yellow crystals (723 g, yield: 94.4%).
$^1$H-NMR (300 MHz, DMSO-d$_6$) δ: 1.32-1.40 (1H, m), 1.62-1.74 (3H, m), 1.82-1.90 (1H, m), 2.28-2.38 (1H, m), 2.74 (6H, s), 2.76-2.82 (3H, br), 3.08-3.16 (2H, m), 5.09 (2H, s), 6.72-6.80 (2H, m), 6.96 (1H, d, J=8.0 Hz), 7.32-7.38 (1H, m), 7.44-7.54 (4H, m), 7.64-7.72 (4H, m), 10.4 (1H, br).

Example 1

In a fluidized-bed granulating dryer, the compound A (160 g), lactose (4064 g) and corn starch (640 g) were mixed uniformly. An aqueous solution, in which hydroxypropylcellulose (160 g) was dissolved, was sprayed to the mixture in the dryer to conduct granulation, and then the mixture was dried in the fluidized-bed granulating dryer. The granules thus obtained were pulverized by a Power-Mill pulverizer with a 1.5 mmΦ punching screen to obtain sifted comminuted powder. The sifted comminuted powder (3894 g) was taken, and corn starch (124 g) and magnesium stearate (12.4 g) were added thereto and mixed to obtain granules for compression. The granules were compressed with a tableting machine with a punch of 7.0 mmΦ at the weight of 130 mg to obtain plain tablets. A solution of hydroxypropylmethylcellulose 2910 and copolyvidone, in which titanium dioxide and yellow iron oxide dispersed, was sprayed onto thus-obtained plain tablets in a film-coating-machine to obtain about 25,000 film-coating-tablets having the formulation as shown in Table 1, each of which contained 4 mg of the compound A per tablet.

TABLE 1

| Ingredients | Amount (mg) |
| --- | --- |
| Compound A | 4.0 |
| Lactose | 101.6 |
| Corn starch | 20.0 |
| Hydroxypropylcellulose | 4.0 |
| Magnesium stearate | 0.4 |
| Plain tablet | 130.0 |
| Hydroxypropylmethylcellulose 2910 | 3.74 |
| Copolyvidone | 0.75 |
| Titanium dioxide | 0.5 |
| Yellow iron oxide | 0.01 |
| Total | 135.0 |

Example 2

In a fluidized-bed granulating dryer, the compound B (2.5 g), lactose (228.8 g) and corn starch (65 g) were mixed uniformly. An aqueous solution, in which 10 g of hydroxypropylcellulose was dissolved, was sprayed to the mixture in the dryer to conduct granulation and then the mixture was dried in the fluidized-bed granulating dryer. The granules thus obtained were pulverized by a Power-Mill pulverizer with a of 1.5 mmΦ punching screen to obtain sifted comminuted powder. The shifted comminuted powder (245 g) was taken, and corn starch (13 g) and magnesium stearate (2.0 g) were added thereto and mixed to obtain granules for compression. The granules were compressed with a tableting machine with a punch of 7.0 mmΦ at the weight of 130 mg to obtain plain tablets. A solution of hydroxypropylmethylcellulose 2910 and copolyvidone, in which titanium dioxide and yellow iron oxide were dispersed, was sprayed onto thus-obtained plain tablets in a film-coating-machine to obtain about 1,200 of film-coating-tablets having the formulation as shown in Table 2, each of which contained 1 mg of the compound B per tablet.

TABLE 2

| Ingredients | Amount (mg) |
|---|---|
| Compound B | 1.0 |
| Lactose | 91.5 |
| Corn starch | 32.5 |
| Hydroxypropylcellulose | 4.0 |
| Magnesium stearate | 1.0 |
| Plain tablet | 130.0 |
| Hydroxypropylmethylcellulose 2910 | 3.74 |
| Copolyvidone | 0.75 |
| Titanium dioxide | 0.5 |
| Yellow iron oxide | 0.01 |
| Total | 135.0 |

Comparative Example 1

In the same manner as in Example 1, film-coating-tablets were manufactured except that polyethylene glycol 6000 (0.75 mg) was used in place of copolyvidone (0.75 mg).

Comparative Example 2

In the same manner as in Example 1, film-coating-tablets were manufactured except that polyethylene glycol 6000 in Comparative Example 1 was not used, Test Example 1

The film-coating-tablets of Example 1, Comparative Example 1 and Comparative Example 2 were stored at 60° C. for 4 weeks and the stability of the compound A in the tablets was confirmed by HPLC with measurement of the content (remaining ratio) of the compound A and the total amount of unknown decomposition products. The results are shown in Table 3.

TABLE 3

| Samples | Measurement | Remaining ratio (%) | Total amount of unknown decomposition products (%) |
|---|---|---|---|
| Example 1 | initiation of storage | 100 | 0.03 |
|  | after stored for 4 weeks | 101.3 | 0.07 |
| Comparative Example 1 | initiation of storage | 100 | — |
|  | after stored for 4 weeks | 98.3 | 2.12 |
| Comparative Example 2 | initiation of storage | 100 | — |
|  | after stored for 4 weeks | 99.5 | 0.06 |

Unit in the table represents percentage (%).
Symbol (—) represents a value less than limit of determination (<0.02%).

As seen from Table 3, it is found that, when the coating film contains polyethylene glycol, the preparation is unstable, whereas, when the coating film contains copolyvidone in place of polyethylene glycol, the preparation shows the same stability as that of the preparation whose coating film does not contain polyethylene glycol.

Example 3

Formulation of the present invention is shown in Table 4.

In a fluidized-bed granulating dryer, the compound C (2.3 g), lactose (222.2 g) and corn starch (50 g) were mixed uniformly. An aqueous solution, in which 9 g of hydroxypropylcellulose was dissolved, was sprayed onto the mixture in the dryer to conduct granulation, and the mixture was dried in the fluidized-bed granulating dryer. The granules thus obtained were pulverized by a Power-Mill pulverizer with a 1.5 mmΦ punching screen to obtain sifted comminuted powder. The sifted comminuted powder (226.8 g) was taken and croscarmellose sodium (12 g) and magnesium stearate (1.2 g) were added thereto and mixed to obtain granules for compression. The thus-obtained granules were compressed with a tableting machine with a punch of 7.5 mmΦ at the weight of 150 mg to obtain plain tablets. A solution of hydroxypropylmethylcellulose 2910 and copolyvidone, in which titanium dioxide and yellow iron oxide were dispersed, was sprayed onto the plain tablets in a film-coating-machine to obtain about 1,500 of film-coating-tablets having the formulation as shown in Table 4, each of which contained 1.15 mg of the compound B per tablet.

TABLE 4

| Ingredients | Amount (mg) |
|---|---|
| Compound C | 1.15 |
| Lactose | 111.1 |
| Corn starch | 25.0 |
| Hydroxypropylcellulose | 4.5 |
| Croscarmellose sodium | 7.5 |
| Magnesium stearate | 0.75 |
| Plain tablet | 150.0 |
| Hydroxypropylmethylcellulose 2910 | 4.464 |
| Copolyvidone | 0.9 |
| Titanium dioxide | 0.6 |
| Iron sesquioxide | 0.036 |
| Total | 156.0 |

Comparative Example 3

In the same manner as in Example 3, film-coating-tablets were manufactured except that polyethylene glycol 6000 (0.9 mg) was used in place of copolyvidone (0.9 mg).

Comparative Example 4

In the same manner as in Example 3, film-coating-tablets were manufactured except that polyethylene glycol 6000 in Comparative Example 3 was not used.

Test Example 2

In the same manner as in Test Example 1, the storage test was conducted.

The results are shown in Table 5.

TABLE 5

Content and measurements results of analogue substance

| Samples | Storage conditions | Remaining ratio (%) | Total amount of analogue substance (%) |
|---|---|---|---|
| Example 3 | initiation of storage | 100 | 0.4 |
| | after stored at 60° C. for one month | 99.8 | 0.4 |
| Comparative Example 3 | initiation of storage | 100 | 0.4 |
| | after stored at 60° C. for one month | 96.0 | 1.7 |
| Comparative Example 4 | initiation of storage | 100 | 0.4 |
| | after stored at 60° C. for one month | 99.3 | 0.5 |

As seen from Table 5, regarding the compound C, likewise, the preparation is unstable when the coating film contains polyethylene glycol, whereas, when the coating film contains copolyvidone in place of polyethylene glycol, the preparation has the same stability as that of the preparation whose coating film does not contain polyethylene glycol.

INDUSTRIAL APPLICABILITY

The preparation of the present invention is stable to light, especially ultraviolet light, and heat and has excellent storage stability. Further, according to the present invention, it is possible to provide various coatings including film coating to a drug without making it unstable. The stabilized preparation thus coated of the present invention has a uniform surface and, therefore, a treatment such as marking, etc., can be easily done and the finishing appearance is beautiful. Furthermore, the pharmaceutical preparation is also useful to prevent bitterness of a drug and does not adhere to the esophageal mucosa upon administration.

The coating agent of the present invention is useful as a raw material containing no polyethylene glycol for manufacturing a preparation having excellent storage stability. In addition, the coating agent is superior in operability because of its excellent strength and expansibility and, therefore, uniform coating can be obtained.

The invention claimed is:

1. A coated tablet for stabilizing (S)—N-[2-(1,6,7,8-tetrahydro-2H-indeno[5,4-b]furan-8-yl)ethyl]propionamide (Compound A) or a pharmaceutically acceptable salt thereof comprising:
 a plain tablet comprises:
  Compound A or a pharmaceutically acceptable salt thereof;
  an excipient wherein the excipient is one or more selected from the group consisting of lactose, corn starch and hydroxypropylcellulose;
  and further
  a lubricant, wherein the lubricant is magnesium stearate; and
 a copolyvidone-containing coating agent, free from polyethylene glycol (PEG) with which the plain tablet is coated, which comprises a water-soluble, film-coating base, wherein the water-soluble film-coating base is hydroxypropylmethylcellulose,
 copolyvidone,
 a light-protecting agent, wherein the light-protecting agent is titanium oxide,
 and further
 a colorant, wherein the colorant is yellow iron oxide wherein the amount of decomposition produces in the coated tablet, as measured using high performance liquid chromatography (HPLC), is less than the amount of decomposition products in an analogous tablet, as measured using HPLC, the analogous tablet comprising an identical amount by weight of polyethylene glycol 6000 (PEG 6000) instead of copolyvidone, after storage of the coated tablet and the analogous tablet under similar storage conditions.

2. The coated tablet according to claim 1, wherein:
 the coating agent is soluble in water;
 the plain tablet comprises from about 0.3 mg to about 10 mg Compound A or a pharmaceutically acceptable salt thereof;
 the plain tablet further comprises a binder;
 and/or
 the water-soluble, film-coating base comprises hydroxypropylmethylcellulose 2910.

3. A method selected from the group consisting of:
 a method for stabilizing (S)—N-[2-(1,6,7,8-tetrahydro-2H-indeno[5,4-b]furan-8-yl)ethyl]propionamide (Compound A) or a pharmaceutically acceptable salt thereof, which comprises coating a plain tablet comprising Compound A or the pharmaceutically acceptable salt thereof;
 an excipient wherein the excipient is one or more selected from the group consisting of lactose, corn starch and hydroxypropylcellulose;
 and further
 a lubricant, wherein the lubricant is magnesium stearate;
 with a polyethylene glycol (PEG)-free, copolyvidone-containing coating agent comprising a water-soluble, film-coating base, wherein the water-soluble, film-coating base is hydroxypropylmethylcellulose, copolyvidone,
 a light-protecting agent, wherein the light-protecting agent is titanium oxide,
 and further
 a colorant, wherein the colorant is yellow iron oxide;
  wherein the amount of decomposition products in the coated tablet, as measured using high performance liquid chromatography (HPLC), is less than the amount of decomposition products in an analogous tablet, as measured using HPLC, the analogous tablet comprising an identical amount by weight of polyethylene glycol 6000 (PEG 6000) instead of copolyvidone, after storage of the coated tablet and the analogous tablet under similar storage conditions.

4. A method of treating or alleviating a biological rhythm disorder comprising administering to a patient in need thereof an effective dose of (S)—N-[2-(1, 6, 7, 8-tetrahydro-2H-indeno[5, 4-b]furan-8-yl)ethyl]propionamide (Compound A) or a pharmaceutically acceptable salt thereof in the coated tablet of claim 1.

5. The method of claim 4, wherein:
 the biological rhythm disorder is a melatonin-influenced disorder;
 the biological rhythm disorder comprises dysgryphia, a sleep-awakening rhythm disorder, jet lag, or time-zone syndrome; and/or the plain tablet comprises from about 0.3 mg to about 10 mg Compound A or a pharmaceutically acceptable salt thereof.

6. The method of claim 3, wherein the plain tablet comprises from about 0.3 mg to about 10 mg Compound A or a pharmaceutically acceptable salt thereof.

7. The method of claim 3, wherein:
the plain tablet comprises from about 0.3 mg to about 10 mg Compound A or a pharmaceutically acceptable salt thereof;
the plain tablet further comprises a binder;
the coating agent is soluble in water; and/or
the water-soluble, film-coating base comprises hydroxypropylmethylcellulose 2910.

8. The method of claim 3, wherein the amount of decomposition products in the analogous tablet is at least twice as much as the amount of decomposition products in the coated tablet after storage of the coated tablet and the analogous tablet for about 4 weeks.

9. The method of claim 3, wherein the amount of decomposition products in the analogous tablet is at least three times as much as the amount of decomposition products in the coated tablet after storage of the coated tablet and the analogous tablet for about 4 weeks.

10. The method of claim 3, wherein the content of Compound A in the coated tablet, as measured using high performance liquid chromatography (HPLC), is substantially the same after storage of the coated tablet as the content of Compound A in the coated tablet prior to storage.

11. The coated tablet according to claim 1, wherein the plain tablet comprises from about 0.3 mg to about 10 mg of Compound A, and the water-soluble, film-coating base is hydroxypropylmethylcellulose 2910.

12. The coated tablet of claim 1, wherein the amount of decomposition products in the analogous tablet is at least twice as much as the amount of decomposition products in the coated tablet after storage of the coated tablet and the analogous tablet for about 4 weeks.

13. The coated tablet of claim 1, wherein the amount of decomposition products in the analogous tablet is at least three times as much as the amount of decomposition products in the coated tablet after storage of the coated tablet and the analogous tablet for about 4 weeks.

14. The coated tablet of claim 1, wherein the content of Compound A in the coated tablet, as measured using high performance liquid chromatography (HPLC), is substantially the same after storage of the coated tablet as the content of Compound A in the coated tablet prior to storage.

15. The coated tablet of claim 2, wherein the content of Compound A in the coated tablet, as measured using high performance liquid chromatography (HPLC), is substantially the same after storage of the coated tablet as the content of Compound A in the coated tablet prior to storage.

* * * * *